US009757016B2

(12) United States Patent
Hirabayashi et al.

(10) Patent No.: US 9,757,016 B2
(45) Date of Patent: Sep. 12, 2017

(54) WIRELESS COMMUNICATION SYSTEM, WIRELESS TERMINAL APPARATUS, AND STORAGE MEDIUM

(71) Applicant: SONY CORPORATION, Tokyo (JP)

(72) Inventors: Takayuki Hirabayashi, Tokyo (JP); Yoichiro Sako, Tokyo (JP); Katsuhiko Nakano, Saitama (JP)

(73) Assignee: Sony Corporation, Tokyo (JP)

( * ) Notice: Subject to any disclaimer, the term of this patent is extended or adjusted under 35 U.S.C. 154(b) by 486 days.

(21) Appl. No.: 14/267,284

(22) Filed: May 1, 2014

(65) Prior Publication Data

US 2014/0378762 A1  Dec. 25, 2014

(30) Foreign Application Priority Data

Jun. 19, 2013  (JP) .................................. 2013-128615

(51) Int. Cl.
  *A61B 1/04*  (2006.01)
  *A61B 1/00*  (2006.01)
  (Continued)

(52) U.S. Cl.
  CPC .......... *A61B 1/045* (2013.01); *A61B 1/00006* (2013.01); *A61B 1/00016* (2013.01);
  (Continued)

(58) Field of Classification Search
  CPC ............ A61B 1/00158; A61B 1/00156; A61B 1/0016; A61B 1/0041; A61B 1/00027
  See application file for complete search history.

(56) References Cited

U.S. PATENT DOCUMENTS 6,036,637 A * 3/2000 Kudo ................. A61B 1/00039
  600/102
2003/0214579 A1 * 11/2003 Iddan ................. A61B 1/00156
  348/81

(Continued)

FOREIGN PATENT DOCUMENTS

JP  2003-325438  11/2003
JP  2008283791 A * 11/2008

OTHER PUBLICATIONS

Machine translation of JP 2008-283791 retrieved from espacenet on Nov. 8, 2016.*

*Primary Examiner* — Alexandra Newton
(74) *Attorney, Agent, or Firm* — Paratus Law Group, PLLC

(57) ABSTRACT

There is provided a wireless communication system including a wireless capsule including an imaging section, a posture control section, a first wireless communication section which transmits an image captured by the imaging section and receives a control signal for controlling the posture control section, and a power supply section which supplies power to the imaging section and the posture control section, and a wireless terminal apparatus including a second wireless communication section which receives the image transmitted from the first wireless communication section, and transmits the control signal, a display control section which performs a control in a manner that the image is displayed on a display section, a posture detection section which detects a posture of the display section, and a generation section which generates the control signal based on a posture signal detected by the posture detection section.

12 Claims, 14 Drawing Sheets

(51) Int. Cl.
*A61B 1/045* (2006.01)
*A61B 5/11* (2006.01)

(52) U.S. Cl.
CPC ...... *A61B 1/00048* (2013.01); *A61B 1/00156* (2013.01); *A61B 1/041* (2013.01); *A61B 5/1116* (2013.01)

(56) References Cited

U.S. PATENT DOCUMENTS

| | | | |
|---|---|---|---|
| 2007/0221233 A1* | 9/2007 | Kawano | A61B 1/00016 128/899 |
| 2012/0098523 A1* | 4/2012 | Iida | A61B 1/00158 324/202 |
| 2013/0204085 A1* | 8/2013 | Alexander | A61B 1/05 600/109 |

* cited by examiner

WIRELESS COMMUNICATION SYSTEM, WIRELESS TERMINAL APPARATUS, AND STORAGE MEDIUM

CROSS REFERENCE TO RELATED APPLICATIONS

This application claims the benefit of Japanese Priority Patent Application JP 2013-128615 filed Jun. 19, 2013, the entire contents of which are incorporated herein by reference.

BACKGROUND

The present disclosure relates to a wireless communication system, a wireless terminal apparatus, and a storage medium.

In recent years, capsule endoscopes with built-in cameras have been proposed. For example, JP 2003-325438A discloses a capsule type medical apparatus which has a camera and illumination function, and a function which releases medicine from an opening section of the capsule.

SUMMARY

However, since movement within the body of a capsule such as described above is performed naturally by movements of the internal organs (peristaltic movements), it will take time to reach an intended affected part, or it will be difficult to control the orientation of the capsule within the body from the outside, and it will be difficult to accurately image the affected part.

Accordingly, the present disclosure proposes a wireless communication system, a wireless terminal apparatus and a storage medium capable of intuitively controlling the posture of a capsule having an imaging function.

According to an embodiment of the present disclosure, there is provided a wireless communication system including a wireless capsule including an imaging section, a posture control section, a first wireless communication section which transmits an image captured by the imaging section and receives a control signal for controlling the posture control section, and a power supply section which supplies power to the imaging section and the posture control section, and a wireless terminal apparatus including a second wireless communication section which receives the image transmitted from the first wireless communication section, and transmits the control signal, a display control section which performs a control in a manner that the image is displayed on a display section, a posture detection section which detects a posture of the display section, and a generation section which generates the control signal based on a posture signal detected by the posture detection section.

According to an embodiment of the present disclosure, there is provided a wireless terminal apparatus including a wireless communication section which receives an image transmitted from a wireless capsule and transmits a control signal which controls a posture of the wireless capsule, a display control section which performs a control in a manner that the image is displayed on a display section, a posture detection section which detects a posture of the display section, and a generation section which generates the control signal based on a posture signal detected by the posture detection section.

According to an embodiment of the present disclosure, there is provided a non-transitory computer-readable storage medium having a program stored therein, the program causing a computer to function as a wireless communication section which receives an image transmitted from a wireless capsule, and transmits a control signal which controls a posture of the wireless capsule, a display control section which performs a control in a manner the image is displayed on a display section, a posture detection section which detects a posture of the display section, and a generation section which generates the control signal based on a posture signal detected by the posture detection section.

According to one or more embodiments of the present disclosure such as described above, it becomes possible to intuitively control the posture of a capsule having an imaging function.

DETAILED DESCRIPTION OF THE EMBODIMENT(S)

Figure 1:
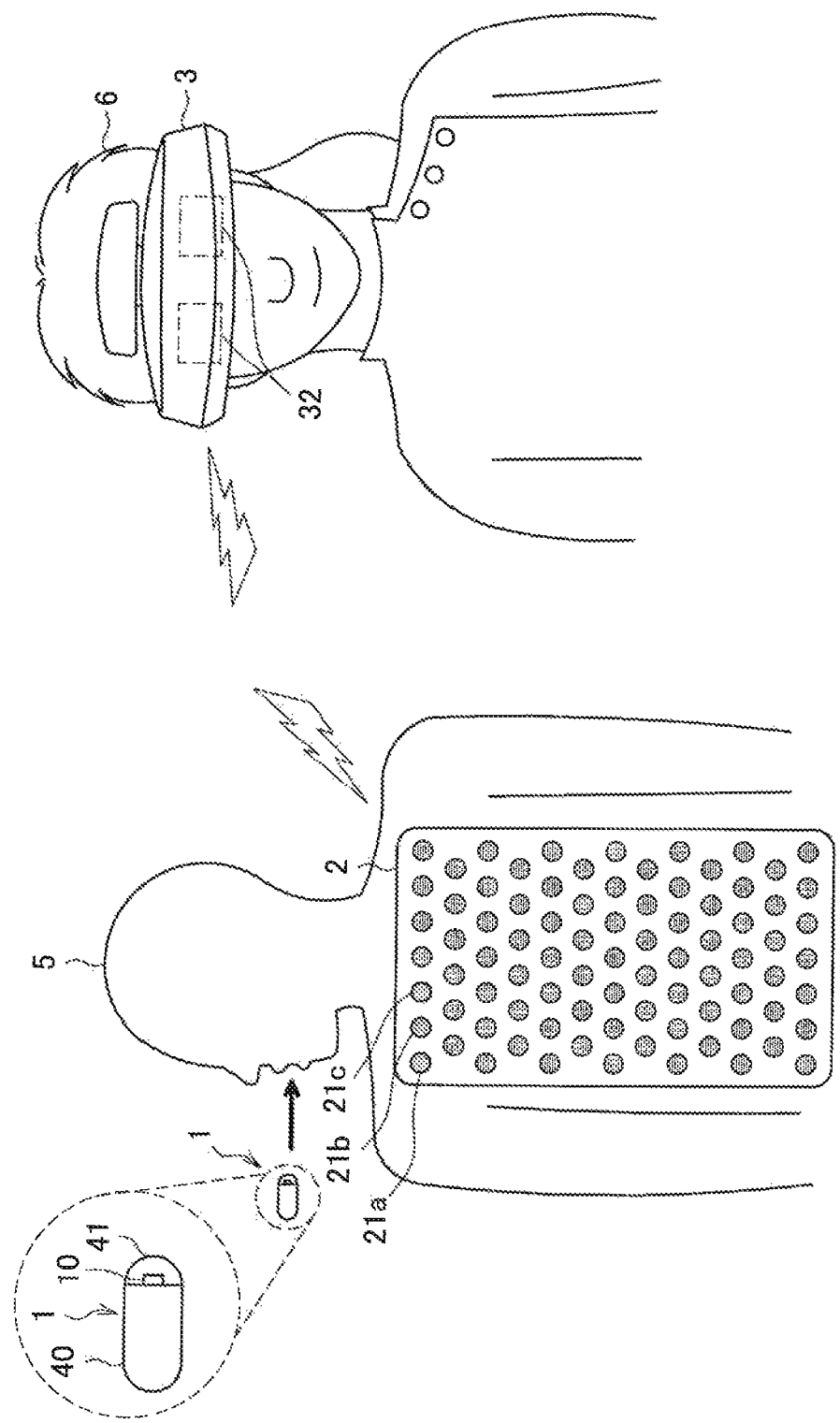
FIG. 1 is a figure for describing an outline of a control system according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.

1. Outline of the control system according to an embodiment of the present disclosure
2. The first embodiment
2-1. Configuration
2-2. Operation processes
3. The second embodiment
3-1. Configuration
3-2. Operation processes
4. Conclusion

1. Outline of the Control System According to an Embodiment of the Present Disclosure First, an outline of a control system according to an embodiment of the present disclosure will be described by referring to FIG. 1. As shown in FIG. 1, a wireless capsule (capsule type medical apparatus) 1 according to the present embodiment is swallowed from the mouth of a test subject 5, and wirelessly transmits an image signal (captured image) which optically captures the tract inner wall surface inside the body cavity when passing through the tract inside the body cavity.

As shown in FIG. 1, for example, the wireless capsule 1 has an approximately cylindrical shape, and is covered by an exterior case 40 closed and rounded at the rear end of the wireless capsule 1. Further, a hemispherical transparent cover 41 is connected and fixed to the front end portion of the exterior case 40 in a watertight manner. As shown in FIG. 1, an imaging section (including an imaging lens) 10 is arranged within a container sealed on the inner side of the transparent cover 41 so as to oppose the transparent cover 41. Note that, an illumination section (not shown in the figures) may be arranged in the surroundings of the imaging section 10.

Further, as shown in FIG. 1, a wireless relay apparatus 2 is worn on the body surface of the test subject 5. A plurality of the wireless communication sections 21 (wireless communication sections 21a, 21b, 21c or the like) are included on the wireless relay apparatus 2. The wireless relay apparatus 2 has a function which relays data communication between the wireless capsule 1 and an HMD (Head Mounted Display) 3 worn by a medical practitioner 6. The wireless communication sections 21 included on the wireless relay apparatus 2 are not limited to the form of being worn on the body surface such as shown in FIG. 1, and may be set at prescribed positions within the body.

The HMD 3 is an example of a wireless terminal apparatus, has a mounting unit with a half-circumferential type frame structure from both sides of the head to the back of the head, for example, and is worn by the medical practitioner 6 by placing on both ears such as shown in FIG. 1. Further, when the HMD 1 is in a worn state, a display section 32 is arranged directly in front of both eyes of the medical practitioner 6. For example, a captured image within the body (hereinafter, called a body interior image), captured by the wireless capsule 1 and transmitted via the wireless relay apparatus 2, is displayed on the display section 32.

Note that, the wireless capsule 1 and the HMD 3 may perform transmission and reception of data directly and not via the wireless relay apparatus 2.

Here, as described above, since movements within the body are performed naturally by movements of the internal organs (peristaltic movements), it will be particularly difficult for a capsule type medical apparatus of the related art to control the orientation of the capsule within the body from the outside, and it will be difficult to accurately image an affected part.

Accordingly, according to the present embodiment, a system is provided in which the posture of the wireless capsule 1 can be intuitively controlled, by displaying a body interior image on the HMD 3, and controlling the posture (specifically, the imaging direction) of the wireless capsule 1, which has an imaging function, in accordance with movements of the HMD 3.

Heretofore, an outline of the control system according to an embodiment of the present disclosure has been described. To continue, the control system (wireless communication system) according to embodiments of the present disclosure will be specifically described by using a plurality of embodiments.

2. The First Embodiment

2-1. Configuration

The control system (wireless communication system) according to a first embodiment includes a wireless capsule 1-1, a wireless relay apparatus 2-1 and an HMD 3-1, and has a function in which the wireless capsule 1-1 transmits a beacon electric wave (specifically, a microwave or the like) for notifying its own position. Hereinafter, a configuration of each of the apparatuses which form the control system (wireless communication system) according to the present embodiment will be specifically disclosed by referring to FIG. 2 to FIG. 6.

2-1-1. Configuration of the Wireless Capsule

Figure 2:
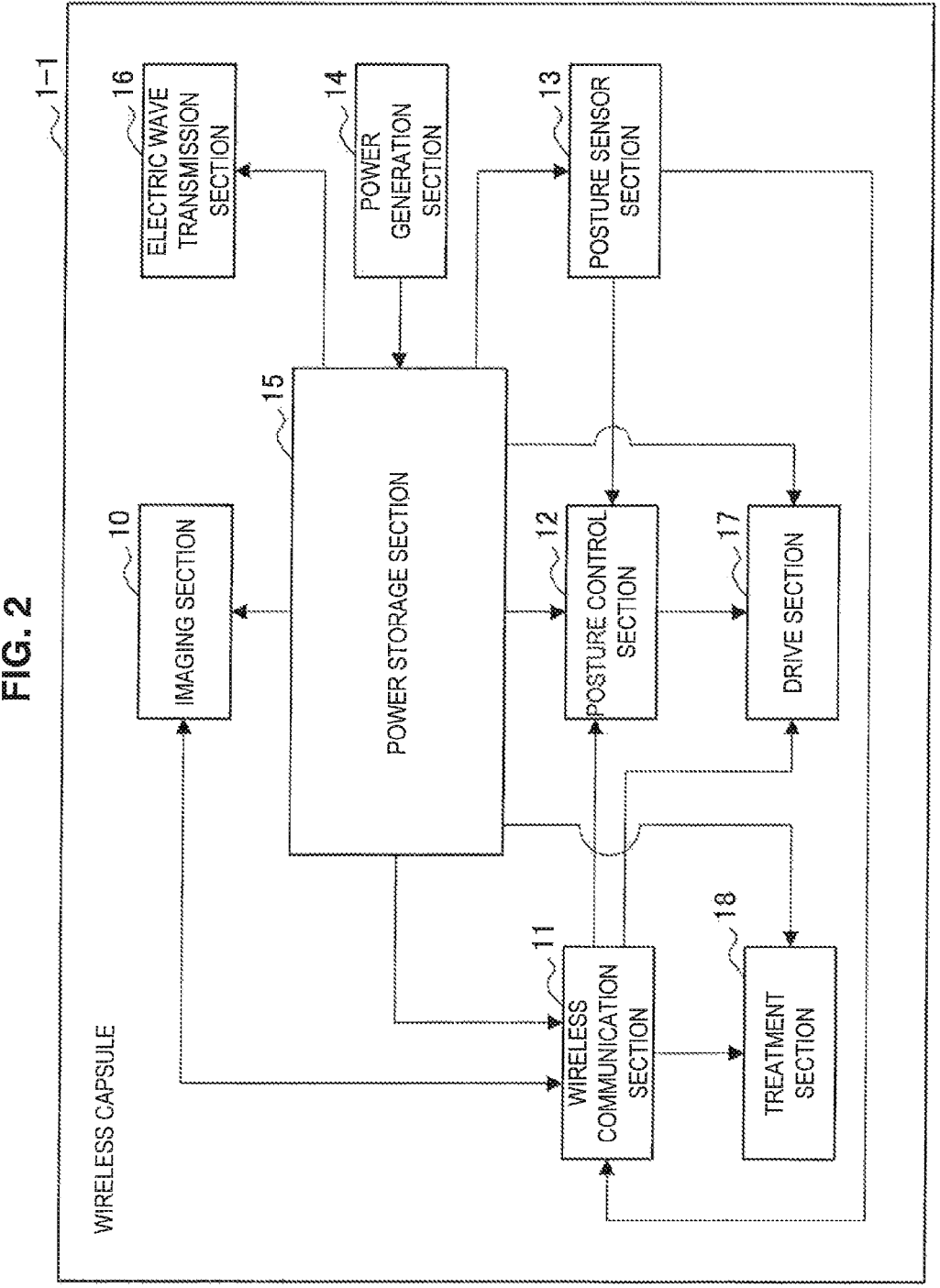
FIG. 2 is a block diagram which shows an example of a configuration of a wireless capsule according to a first embodiment of the present disclosure.

FIG. 2 is a block diagram which shows an example of a configuration of the wireless capsule 1-1 according to the first embodiment. As shown in FIG. 2, the wireless capsule 1-1 according to the present embodiment has an imaging section 10, a wireless communication section 11 (first wireless communication section), a posture control section 12, a posture sensor section 13, a power generation section 14, a power storage section 15, an electric wave transmission section 16, a drive section 17, and a treatment section 18.

As shown in FIG. 1, the imaging section 10 is arranged inside the transparent cover 41, and images inside the body cavity tract when the wireless capsule 1-1 moves within the body. Note that, the imaging section 10 may be configured to be independently moveable such that the imaging direction is changeable up and down, left and right or the like. In this way, an affected part can be more accurately imaged, by changing the direction of the imaging section 10 (at least an imaging lens is included in the imaging section 10), without changing the direction of the wireless capsule 1-1 main body.

The wireless communication section 11 (first wireless communication section) wirelessly connects to the wireless relay apparatus 2-1, which is worn on the body surface of the test subject 5, or the HMD 3-1, and performs transmission and reception of data. For example, the wireless communication section 11 transmits a body interior image captured by the imaging section 10 to the HMD 3-1 via the wireless relay apparatus 2. Further, the wireless communication section 11 receives control signals for controlling the posture control section 12, which will be described later, from the HMD 3-1 via the wireless relay apparatus 2-1.

The posture control section 12 has a function which controls the posture of the wireless capsule 1 main body or the independently moveable type imaging section 10, in accordance with control signals received by the wireless communication section 11, and a function which turns the imaging direction towards an arbitrary direction. For example, a control of the posture of the wireless capsule 1 main body can be implemented by controlling the drive section 17, which will be described later. Further, the posture control section 12 controls the wireless capsule 1-1 in a posture (imaging direction) in accordance with the above described control signals, by referring to posture signals of the wireless capsule 1-1 main body 1-1 detected by the posture sensor section 13.

The posture sensor section 13 has a function which detects the posture of the wireless capsule 1-1 main body. The posture sensor section 13 outputs the detected posture signals from the wireless communication section 11 to the HMD 3-1 and/or the posture control section 12. Further, for example, the posture sensor section 13 is implemented by a three-axis acceleration sensor. Further, the posture sensor section 13 additionally includes a gyro sensor, and can detect more accurate posture signals.

The power generation section 14 has a function which generates power, and sends the generated power to the power storage section 15. For example, the power generation section 14 receives power transmitted from the wireless power supply section 22 of the wireless relay apparatus 2-1, by an electric wave system, an electric field coupling system, an electromagnetic induction system, or a magnetic field resonance system. For example, as will be described later, the power generation section 14 may be implemented by a plurality of rectifying antennas which generate power by resonating at electric waves of a plurality of different frequencies.

Further, the power generation section 14 is not limited to wireless power supply from the outside (the wireless relay apparatus 2-1), and may be implemented by a battery capable of generating power by itself. For example, the power generation section 14 may generate power which uses body fluids as an electrolyte, or may generate power via a MEMS gyro or the like by movement energy (acceleration) of peristaltic movements (natural movements).

The power storage section 15 has a function which charges power generated by the power generation section 14. The power storage section 15 supplies power to each of the elements of the wireless capsule 1-1.

The electric wave transmission section 16 has a function which transmits electric waves such as microwaves, and continuously transmits electric waves. These electric waves are used when estimating the position of the wireless capsule 1-1, which will be described later.

The drive section 17 has a function (self-propulsion function) which moves the wireless capsule 1-1 within the body, and is implemented, for example, by a micro-motor, a caterpillar, or a spiral type member (screw member). In this way, the wireless capsule 1-1 according to the present embodiment can quickly reach up to an affected part by natural movements due to peristaltic movements.

Further, the drive section 17 may perform drive controls in accordance with control signals received, by the wireless communication section 11, from the HMD 3-1 via the wireless relay apparatus 2-1. For example, since control signals which perform instructions so as to increase the movement speed are transmitted from the HMD 3-1 when the wireless capsule 1 has moved to a portion which is far from the affected part, the drive section 17 performs drive controls so as to move quickly in accordance with these control signals. In this way, the overall examination/treatment time by the wireless capsule 1 can be shortened.

Further, the drive section 17 is not partially self-propelled, but can implement energy savings by taking advantage of peristaltic movements as well to move.

Further, a plurality of the drive sections 17 can be included in the wireless capsule 1-1 according to the present embodiment, and the posture of the wireless capsule 1-1 can be controlled, by driving in accordance with a control by the posture control section 12. An arrangement example of the plurality of drive sections 17 will be described by referring to FIG. 3 and FIG. 4.

Figure 3:
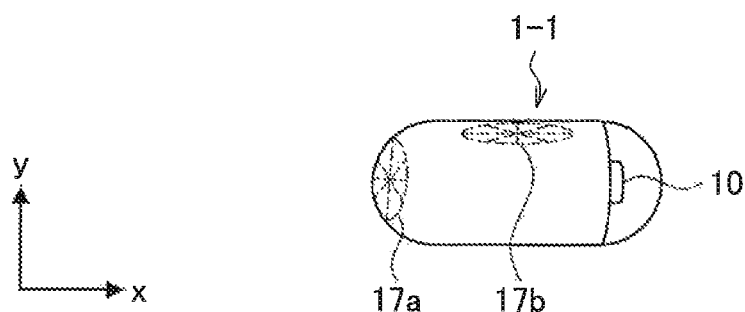
FIG. 3 is a figure for describing an arrangement of a plurality of drive sections according to the first embodiment.

FIG. 3 is a figure for describing an arrangement of a plurality of drive sections 17a and 17b according to the first embodiment. As shown in FIG. 3, for example, the drive sections 17a and 17b formed by micro-motors (for example, MEMS: Micro Electro mechanical Systems) may be arranged in two axial directions of the wireless capsule 1. In this case, the posture control section 12 can control the direction (posture) of the wireless capsule 1-1, by driving at least one of the drive sections 17a and 17b.

Further, the shape of the wireless capsule 1-1 according to the present embodiment is not limited to an approximately cylindrical shape such as shown in FIG. 3, and may be a spherical shape, for example. Here, an arrangement of the plurality of drive sections 17 in a spherical wireless capsule 1-1' will be described by referring to FIG. 4.

Figure 4:
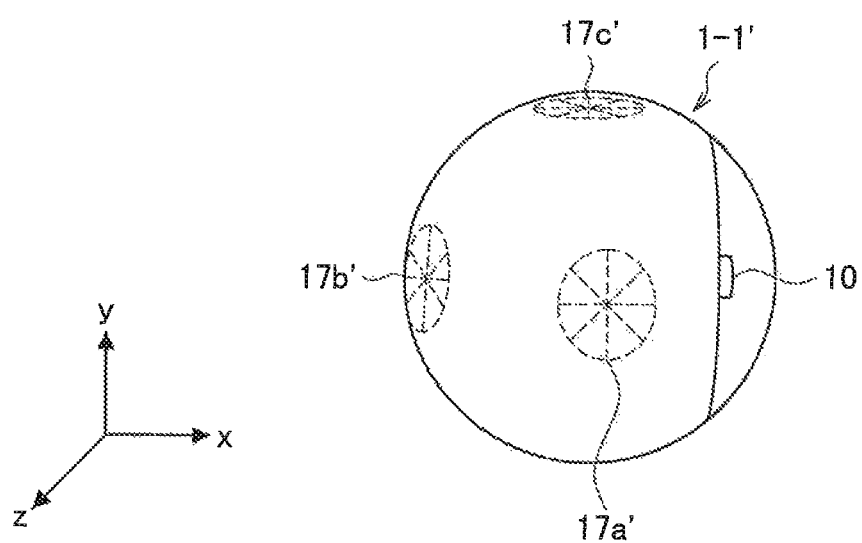
FIG. 4 is a figure for describing an arrangement of a plurality of drive sections according to a modified example of the first embodiment.

FIG. 4 is a figure for describing an arrangement of a plurality of drive sections 17a', 17b' and 17c' according to a modified example of the first embodiment. As shown in FIG. 4, for example, the drive sections 17a', 17b' and 17c' formed by micro-motors may be arranged in three axial directions of the wireless capsule 1-1'. In this case, the posture control section 12 can control the direction (posture) of the wireless capsule 1-1', by driving at least one of the drive sections 17a', 17b' and 17c'.

In this way, in the case where a plurality of drive sections 17 are included in the wireless capsule 1-1, the posture control section 12 can control the direction (posture) of the wireless capsule 1-1 main body by using the plurality of drive sections 17. Note that, a plurality of power generation sections 14 which supply power are respectively included in each of the plurality of drive sections 17, and the plurality of power generation sections 14 may be implemented by a plurality of rectifying antennas which generate power by resonating at electric waves of a plurality of different frequencies. In this case, the plurality of drive sections 17 are driven in accordance with the different frequencies transmitted from the wireless relay apparatus 2-1, and posture control is substantially implemented. At this time, the wireless relay apparatus 2-1 performs power transmission at electric waves of different frequencies, so as to control the posture of the wireless capsule 1-1 in accordance with control signals from the HMD 3-1.

The treatment section 18 has a function which performs a prescribed treatment for an affected part in accordance with control signals received by the wireless communication section 11. Specifically, for example, the treatment section 18 releases medicine, emits microwaves, or cuts the affected part. Further, in the case where it may be necessary to perform treatment by temporarily stopping near the affected part, the wireless capsule 1-1 main body is stopped by a stopping section (not shown in the figures) which can stop at a prescribed position inside the body cavity, by sandwiching the inner wall near the affected part and expanding a balloon which has an airtight function with free expansion/contraction.

Heretofore, a configuration of the wireless capsule 1-1 according to the first embodiment has been described. Note that, the configuration shown in FIG. 2 is an example, and the configuration of the wireless capsule 1-1 is not limited to the example shown in FIG. 2. For example, the wireless capsule 1-1 may have a configuration which does not have the drive section 17 and the treatment section 18.

2-1-2. Configuration of the Wireless Relay Apparatus

Figure 5:
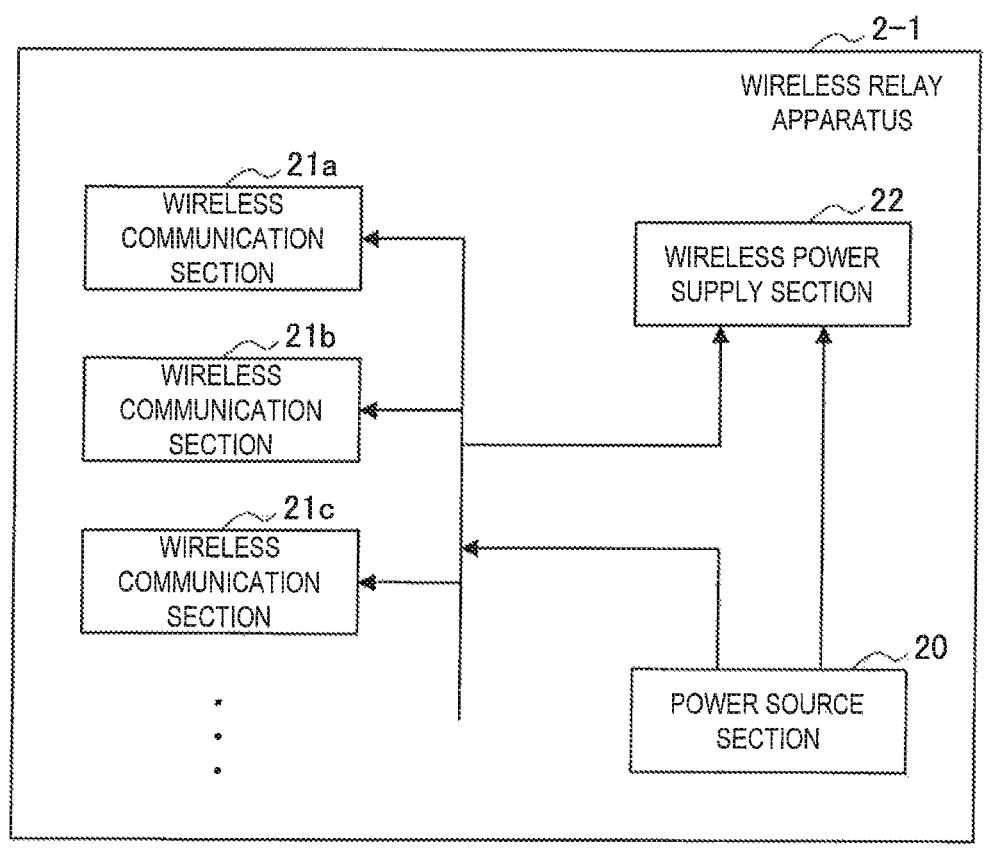
FIG. 5 is a block diagram which shows an example of a configuration of a wireless relay apparatus according to the first embodiment.

FIG. 5 is a block diagram which shows an example of a configuration of the wireless relay apparatus 2-1 according to the first embodiment. As shown in FIG. 5, the wireless relay apparatus 2-1 according to the present embodiment has a power source section 20, a plurality of wireless communication sections 21a, 21b and 21c (hereinafter, called a plurality of wireless communication sections 21), and a wireless power supply section 22.

The power source section 20 controls the power supply ON/OFF of the wireless relay apparatus 2-1, and has a function which supplies power to each of the elements in the case where the power supply is turned ON. For example, power supply ON/OFF can be controlled in accordance with user operations.

The plurality of wireless communication sections 21 (third wireless communication sections) have a function which performs data transmission and reception with the wireless capsule 1-1, and performs data transmission and reception with the HMD 2. For example, the plurality of wireless communication sections 21 receive a body interior image from the wireless capsule 1-1 and transmit the received body interior image to the HMD 3-1, and receive control signals from the HMD 3-1 (for example, control signals which instruct a posture control of the wireless capsule 1-1 main body) and transmits the received control signals to the wireless capsule 1-1. In this way, the wireless relay apparatus 2-1 according to the present embodiment can perform a relay of data communication between the wireless capsule 1-1 and the HMD 3-1.

Further, the plurality of wireless communication sections 21 receive electric waves continuously transmitted from the electric wave transmission section 16 of the wireless capsule 1-1, and transmit information of the received electric waves (intensities and/or phases) to the HMD 3-1. The position within the body of the wireless capsule 1-1 is estimated at the HMD 3-1 side, based on this information of electric waves. Note that, the plurality of wireless communication section 21 may perform mutual transmission and reception of electric waves, and may output these to the HMD 3-1 along with the received electric wave information, and as a result, electric wave propagation characteristics between the plurality of wireless communication sections 21, which will be described later, are measured on the HMD 3-1 side, and the position of the wireless capsule 1-1 is more accurately estimated.

The wireless power supply section 22 performs wireless power supply to the wireless capsule, in accordance with control signals (for example, control signals which instruct power supply) received from the HMD 2 by the wireless communication section 21. For example, the wireless power supply section 22 transmits (supplies) power, by an electromagnetic induction system, an electric wave system or an electromagnetic field resonance system.

Further, the wireless power supply section 22 may perform power supply by electric waves of a plurality of different frequencies in accordance with control signals, received from the HMD 2, which instruct a posture control of the wireless capsule 1-1. In this way, the plurality of drive sections 17 of the wireless capsule 1-1 (refer to FIG. 3 and FIG. 4) are each driven, and the posture of the wireless capsule 1-1 is controlled.

2-1-3. Configuration of the HMD

Figure 6:
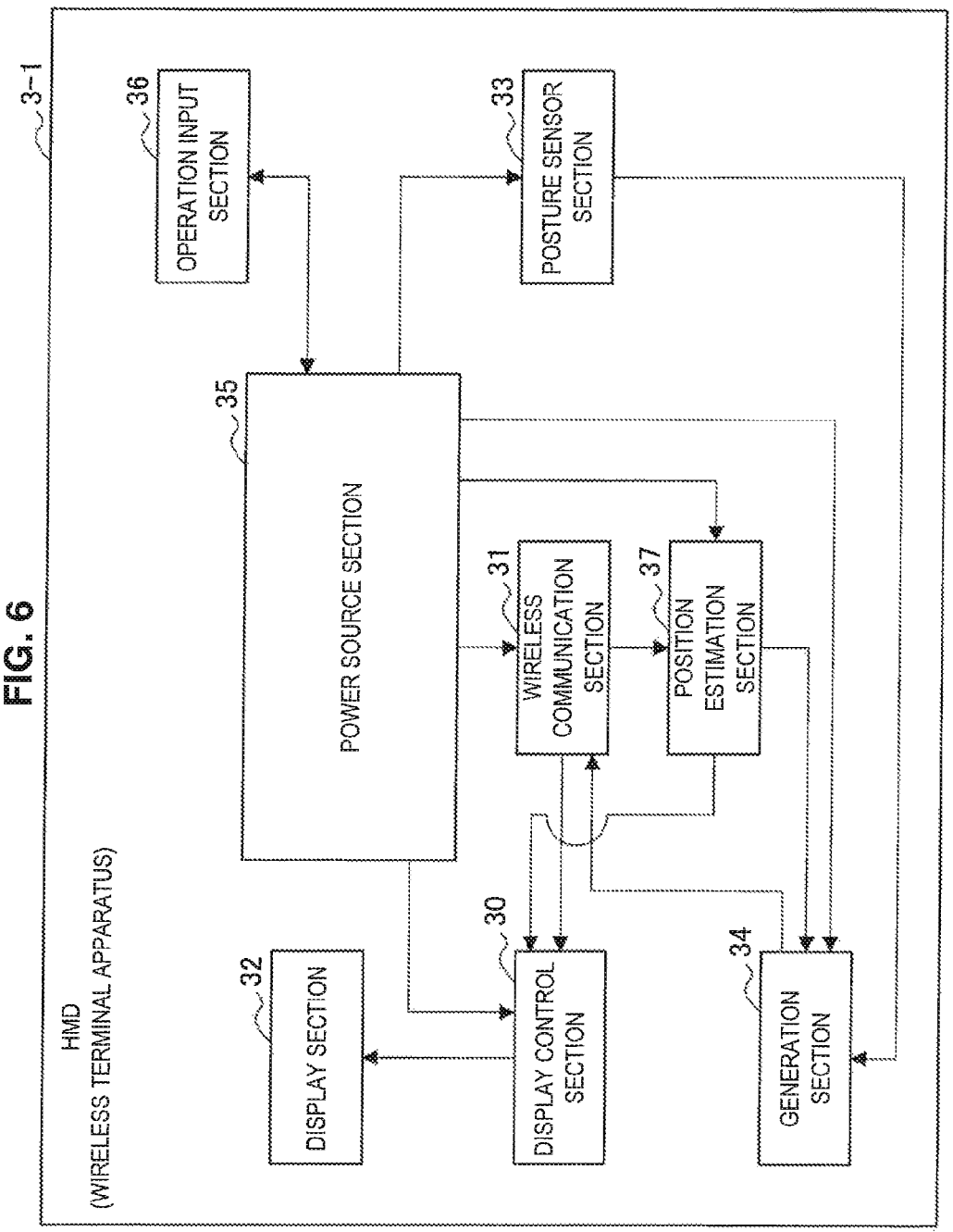
FIG. 6 is a block diagram which shows an example of a configuration of an HMD according to the first embodiment.

FIG. 6 is a block diagram which shows an example of a configuration of the HMD 3-1 according to the first embodiment. As shown in FIG. 6, the HMD 3-1 according to the present embodiment has a display control section 30, a wireless communication section 31 (second wireless communication section), a display section 32, a posture sensor section 33, a generation section 34, a power source section 35, an operation input section 36, and a position estimation section 37.

The display section 32 has a configuration which is arranged directly in front of both eyes of the medical practitioner 6 in a state in which the HMD 3-1 is worn by the medical practitioner 6. The display section 32 has a function which displays a screen which includes images or text, in accordance with a control of the display control section 30. Further, the display section 32 may be implemented by an LCD (Liquid Crystal Display), an OLED (Organic Light-Emitting Diode), a CRT (Cathode Ray Tube) or the like.

The display control section 30 performs a display control of the display section 32. For example, the display control section 30 performs a control so that the wireless communication section 31 displays a body interior image received from the wireless capsule 1-1 via the wireless relay apparatus 2-1. Further, the display control section 30 performs a control so as to display an image which shows the position within the body of the wireless capsule 1-1 estimated by the position estimation section 37. A specific example of images displayed on the display section 32 will be described later by referring to FIG. 10.

The wireless communication section 31 (second communication section) wirelessly connects to the wireless relay apparatus 2-1 or the wireless capsule 1-1, and performs transmission and reception of data. Specifically, for example, the wireless communication section 31 receives a body interior image from the wireless capsule 1-1 via the wireless relay apparatus 2-1, and receives electric wave information (intensities and/or phases of electric waves received from the wireless capsule 1 or the like) from the wireless communication section 31. The wireless communication section 31 outputs the received body interior image to the display control section 30, and outputs the received electric wave information to the position estimation section 37.

Further, the wireless communication section 31 transmits each of the control signals generated by the generation section 34, such as control signals for controlling the wireless power supply section 22 of the wireless relay apparatus 2-1 and control signals for controlling the posture of the wireless capsule 1-1.

The posture sensor section 33 functions as a posture detection section which detects the posture of the HMD 3-1 main body or the posture of the display section 32. Specifically, in the case where the HMD 3-1 and the display section 32 are one body, since the medical practitioner 6 intuitively controls the posture of the wireless capsule 1-1 by moving his or her head while viewing a body interior image displayed on the display section 32, the posture sensor section 33 may detect the posture of the HMD 3-1 main body.

For example, the posture sensor section 33 is implemented by a three-axis acceleration sensor. Further, the posture sensor section 33 additionally includes a gyro sensor, and can detect more accurate posture signals.

Here, the HMD 3-1 is an example of a wireless terminal apparatus according to an embodiment of the present disclosure, and the wireless terminal apparatus according to an embodiment of the present disclosure is not limited to a wearable apparatus on the head such as shown in FIG. 1. For example, the wireless terminal apparatus may be formed from a glasses type display device in which the display section 32 is included on a lens portion, and an information processing apparatus (for example, a PC, a tablet terminal, a smartphone or the like) which connects to this display device by being placed in the surroundings of the medical practitioner 6. In this case, since the medical practitioner 6 intuitively controls the posture of the wireless capsule 1-1 by moving his or her head while viewing a body interior image displayed on the display section 32, the posture sensor section 33 acquires posture signals of the display section 32 by receiving the posture signals from the glasses type display device.

Figure 7:
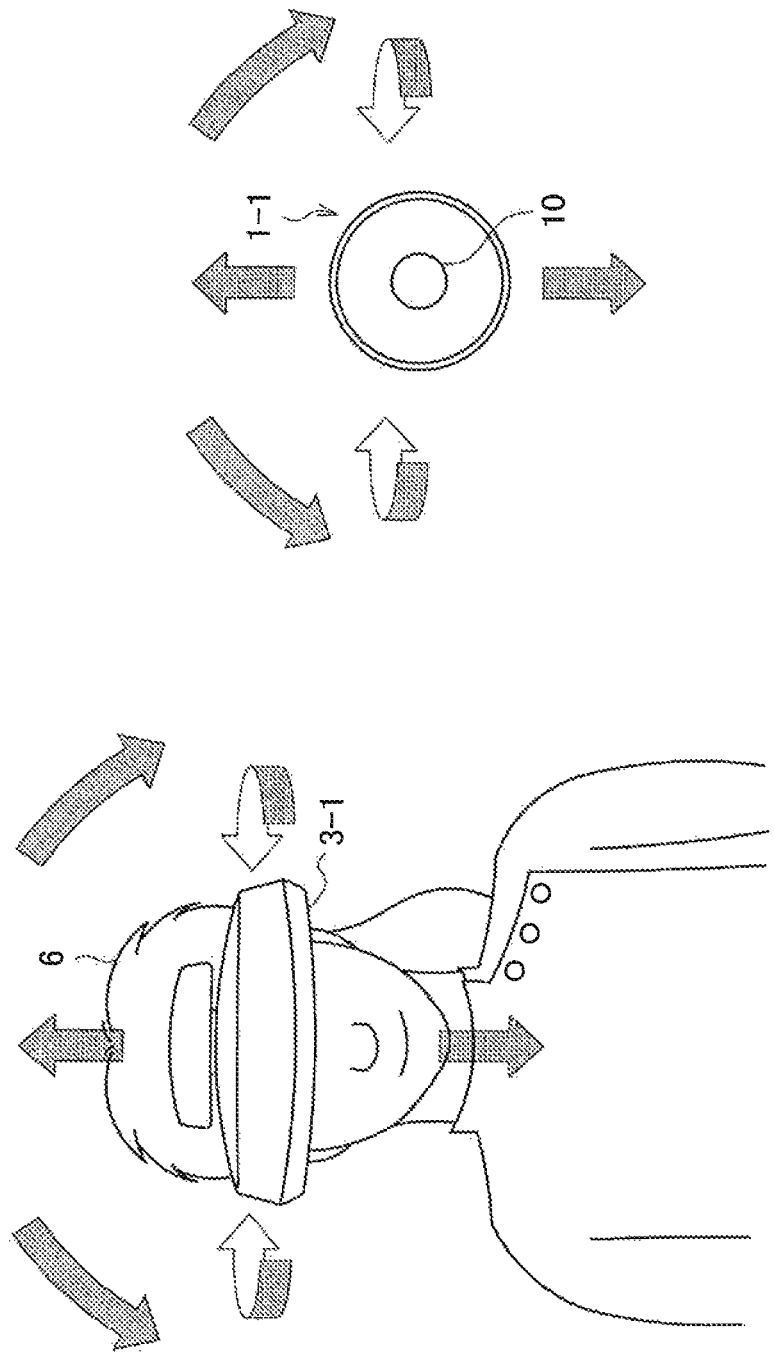
FIG. 7 is a figure for describing a case in which the posture of the wireless capsule is controlled substantially the same as a posture change of the HMD.

The generation section 34 generates control signals for controlling the posture control section of the wireless capsule 1-1, based on the posture signals detected by the posture sensor section 33. Specifically, for example, the generation section 34 generates control signals for controlling the posture of the wireless capsule 1-1 or the imaging section 10 included in the wireless capsule 1-1, in a direction the same as the direction of a change in posture shown by the posture signals detected by the posture sensor section 33. FIG. 7 is a figure for describing a case in which the posture of the wireless capsule 1-1 is controlled to be substantially the same as a posture change of the HMD 3-1.

As shown in FIG. 7, the posture of the wireless capsule 1-1 can be intuitively controlled in real time, by having the medical practitioner 6 move or rotate his or her head up and down or left and right, while viewing a body interior image (an image within the body cavity captured by the imaging section 10 of the wireless capsule 1-1) displayed on the display section 32 of the HMD 3-1 worn on his or her head. For example, when the medical practitioner 6 moves his or her head to the right in order to more accurately observe an affected part in the affected part surroundings, the posture sensor section 33 of the HMD 3-1 detects a posture change in the right direction. Next, the generation section 34 generates control signals for performing instructions so as to perform posture control in the right direction, based on the posture change in the right direction detected by the posture sensor section 33, and transmits the generated control signals from the wireless communication section 31 to the wireless capsule 1-1 via the wireless relay apparatus 2-1. The posture control section 12 of the wireless capsule 1-1 controls the posture of the wireless capsule 1-1 in the right direction by controlling the drive section 17, based on the control signals received by the wireless communication section 11.

Here, the control signals generated by the generation section 34 are not limited to those which are usually synchronized with the posture signals detected by the posture sensor section 33 (movements of the HMD 3-1). For example, in the case where the medical practitioner 6 turns to the right for some time, the generation section 34 may generate control signals which perform instructions so that the wireless capsule 1-1 performs posture conversion in the right direction and afterwards proceeds forward. Further, at the time when the medical practitioner 6 turns once to the right and then returns his or her face to the front, the generation section 34 generates control signals which perform instructions so that the wireless capsule 1-1 performs posture conversion in the right direction as it is.

Further, the generation section 34 generates control signals for controlling movement (driving) of the wireless capsule 1-1. For example, in the case where the position within the body of the wireless capsule 1-1 estimated by the position estimation section 37 is far from an affected part, the generation section 34 generates control signals which perform instructions so as to increase the movement speed.

Further, the generation section 34 generates control signals for controlling imaging by the imaging section 10 of the wireless capsule 1-1. For example, in the case where the position within the body of the wireless capsule 1-1 estimated by the position estimation section 37 is in the surroundings of an affected part, the generation section 34 generates control signals which perform instructions so as to start imaging.

Further, the generation section 34 generates control signals for controlling the treatment section 18 of the wireless capsule 1-1. For example, in the case where the position within the body of the wireless capsule 1-1 estimated by the position estimation section 37 is in the surroundings of an affected part, the generation section 34 generates control signals which perform instructions so as to start a prescribed treatment.

Further, the generation section 34 generates control signals for instructing wireless power supply to the wireless capsule 1-1 by the wireless power supply section 22 of the wireless relay apparatus 2-1.

In this way, the generation section 34 according to the present embodiment generates control signals for performing each of the controls of the wireless capsule 1-1 and the wireless relay apparatus 2-1 (posture control, drive control, imaging control, treatment control, power supply control or the like), and outputs the generated control signals to the wireless communication section 31.

The position estimation section 37 estimates the position within the body of the wireless capsule 1-1, based on the electric wave information (information which shows intensities and/or the phase of the electric waves) received by the wireless communication section 31 from the wireless relay apparatus 2-1. Specifically, for example, the plurality of wireless communication sections 21 of the wireless relay apparatus 2-1 receive electric waves continuously transmitted by the wireless capsule 1-1, and the position estimation section 37 estimates a relative position of the wireless capsule 1-1 with respect to the plurality of wireless communication sections 21 based on each type of acquired electric wave information. Also, in the case where the positions of the plurality of wireless communication sections 21 are already known, the position estimation section 37 can estimate the position within the body of the wireless capsule 1-1.

In this case, the position estimation section 37 can more accurately estimate the position of the wireless capsule 1-1, by using a transfer function within the body corresponding to electric wave propagation characteristics between the plurality of wireless communication sections 21, based on the electric wave information received by the plurality of wireless communication sections 21 performing mutual transmission and reception of electric waves. For example, the position estimation section 37 compares a transfer function within the body of the test subject 5 measured prior to introducing the wireless capsule 1-1 into the test subject 5, and a transfer function within the body of the test subject 5 measured after the wireless capsule 1-1 has been introduced, and extracts a change (difference) in the transfer function. The position estimation section 37 understands the relative position of the wireless capsule 1-1 estimated by the change (difference) in the transfer function within the body of the test subject 5. Also, the position estimation section 37 compares a relative position of the wireless capsule 1-1 estimated by the change in the transfer function within the body, and a relative position of the wireless capsule 1-1 estimated based on the above described information of electric waves from the wireless capsule 1-1, and performs a correction of the estimated position.

The position estimation section 37 transmits information of the estimated position to the generation section 34 and the display control section 30.

The operation input section 36 has a function which detects user operations and a function which receives operation inputs. For example, the operation input section 36 receives an ON/OFF operation of the power source section 35. Further, the operation input section 36 receives a treatment start instruction, a display screen switching instruction or the like, and outputs input user operation information to the generation section 34 and the display control section 30.

The power source section 35 has a function which performs power supply to each of the elements of the HMD 3-1.

Heretofore, a configuration of each of the apparatuses which form the control system (wireless communication system) according to the present embodiment has been described in detail. To continue, the operation processes of the control system according to the present embodiment will be described.

2-2. Operation Processes

The wireless capsule 1-1 according to the present embodiment can be used during examination which is intended to search for an affected part, or can be used during treatment intended for treatment in the case where an affected part has already been discovered (the position of the affected part is already known). Accordingly, hereinafter, the operation processes during examination will be described by referring to FIG. 8, and to continue, the operation processes during treatment will be described by referring to FIG. 9.

2-2-1. During Examination

Figure 8:
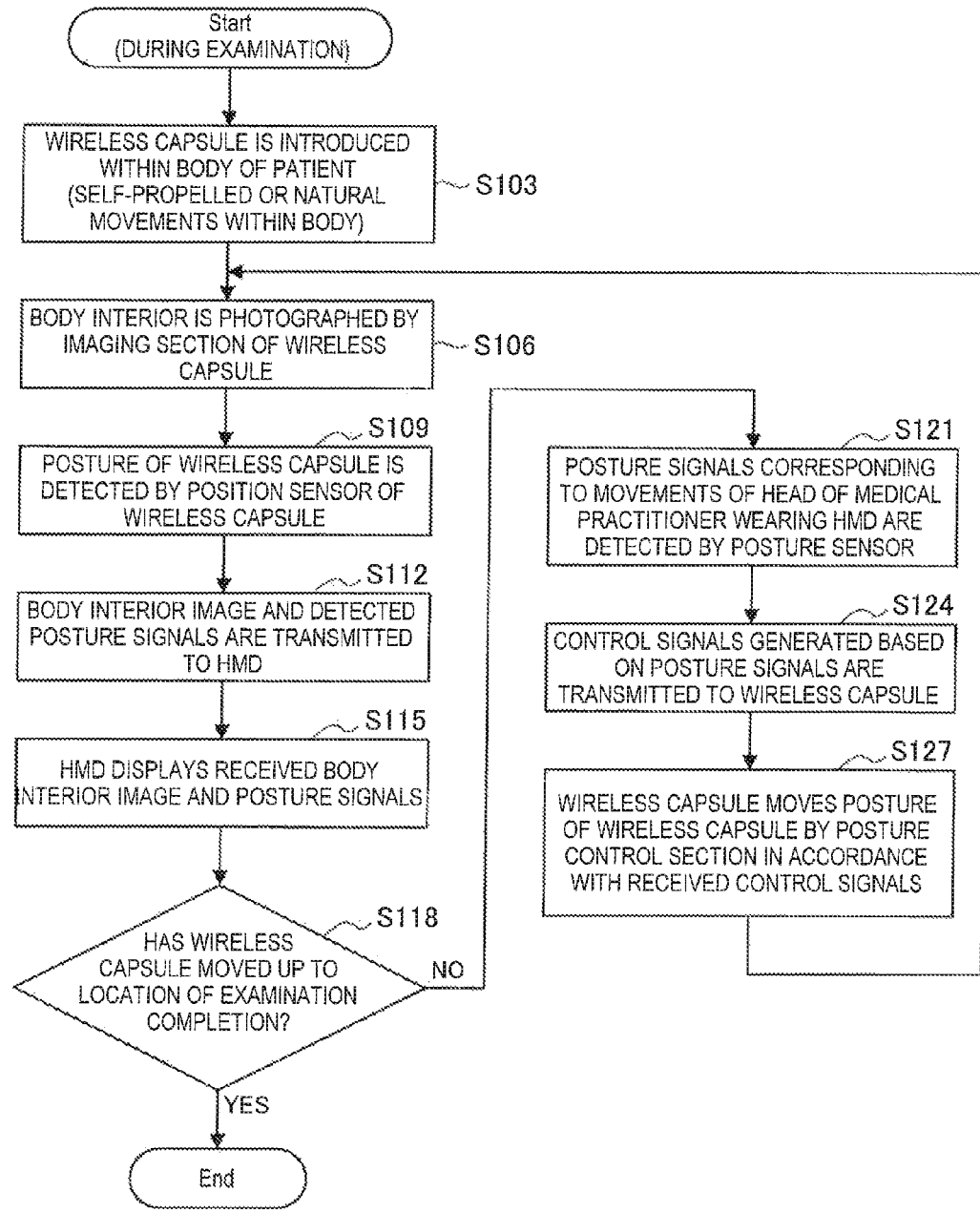
FIG. 8 is a flow chart which shows the operation processes during examination of the control system according to the first embodiment.

FIG. 8 is a flow chart which shows the operation processes during examination of the control system according to the first embodiment. As shown in FIG. 8, first in step S103, the wireless capsule 1-1 is introduced within the body of a patient (the test subject 5), and is self-propelled or naturally moves due to peristaltic movements within the body.

Next, in step S106, the wireless capsule 1-1 photographs within the body by the imaging section 10 while moving within the body. Note that, for example, there are cases where self-propulsion or a trigger of imaging start of the wireless capsule 1-1 is turned ON by a switch (not shown in the figures) of the wireless capsule 1-1, is applied by pressure from the outside of the entire wireless capsule 1-1 (applied by pressure from the tongue or teeth within the mouth), or is transmitted by power from the wireless relay apparatus 2-1.

Next, in step S109, the wireless capsule 1-1 detects the posture of the wireless capsule 1-1 main body by the posture sensor section 13.

Next, in step S112, the wireless capsule 1-1 transmits, by the wireless communication section 11, a body interior image photographed by the imaging section 10 and posture signals detected by the posture sensor section 13 to the HMD 3-1 via the wireless relay apparatus 2-1.

Next, in step S115, the HMD 3-1 receives the body interior image and posture signals by the wireless communication section 31, and displays, by the display control section 30, the present posture (orientation) within the body of the wireless capsule 1-1 on the display section 32, based on the body interior image and the posture signals. In this way, the medical practitioner 6 who is wearing the HMD 3-1 can perform an examination by confirming the body interior image of the test subject 5 (patient) in real time. Further, since the posture within the body of the wireless capsule 1-1 is presented, the medical practitioner 6 can easily confirm what direction the presently displayed body interior image is facing.

To continue, in the case where the wireless capsule 1-1 has not moved up to a location of examination completion (S118/NO), in step S121, the HMD 3-1 detects posture signals corresponding to movements of the head of the medical practitioner, who is wearing the HMD 3-1 main body, by the posture sensor section 33.

Next, in step S124, the generation section 34 of the HMD 3-1 generates control signals for controlling the posture of the wireless capsule 1-1, based on the posture signals detected by the posture sensor section 33, and transmits the generated control signals from the wireless communication section 31 to the HMD 3-1 via the wireless relay apparatus 2-1.

Then, in step S127, the posture control section 12 of the wireless capsule 1-1 controls the posture of the wireless capsule 1-1 main body, in accordance with the control signals received by the wireless communication section 11. In this way, since the medical practitioner 6 can intuitively control the posture of the wireless capsule 1-1 in real time, by moving his or head the head on which the HMD 3-1 is worn, the medical practitioner 6 can more accurately perform an examination within the body.

The above described steps S106 to S115 and S121 to S127 are repeated up until the wireless capsule 1-1 moves to a location of examination completion in step S118. Whether or not the wireless capsule 1-1 has moved to a location of examination completion may be instructed from the HMD 3-1 by a judgment of the medical practitioner 6, or in the case where the position within the body of the wireless capsule 1-1 is automatically estimated, the generation section 34 of the HMD 3-1 may generate control signals which instruct examination completion (imaging stop), and may transmit the generated control signals to the wireless capsule 1-1.

2-2-2. During Treatment

Figure 9:
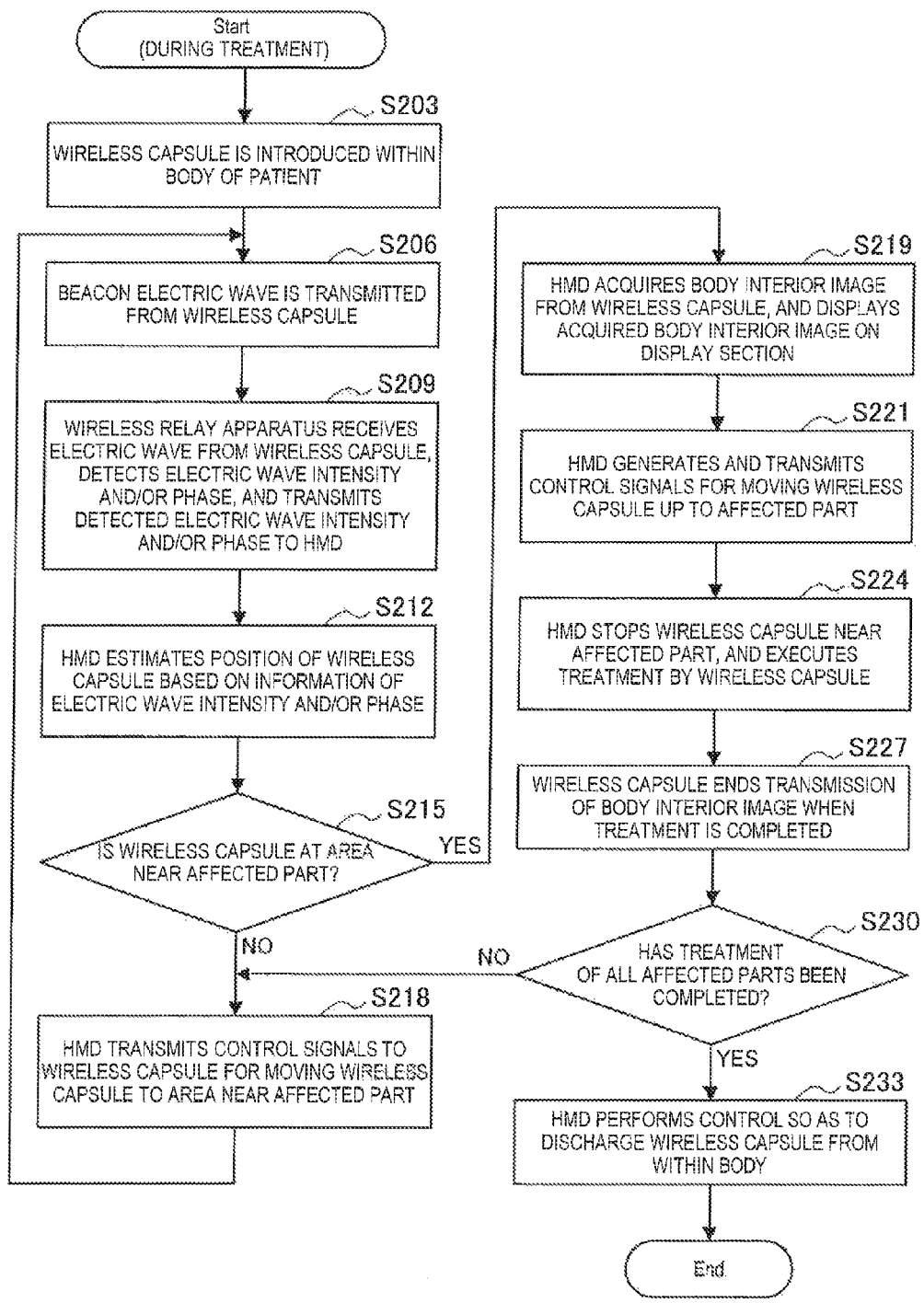
FIG. 9 is a flow chart which shows the operation processes during treatment of the control system according to the first embodiment.

Next, the operation processes of the control system during treatment will be described. Here, it will be assumed that the position of an affected part is already known. FIG. 9 is a flow chart which shows the operation processes during treatment of the control system according to the first embodiment. As shown in FIG. 9, first in step S203, the wireless capsule 1-1 is introduced within the body of a patient (the test subject 5).

Next, in step S206, the electric wave transmission section 16 of the wireless capsule 1-1 transmits a beacon electric wave while moving within the body.

Next, in step S209, the wireless relay apparatus 2-1 receives the beacon electric wave from the wireless capsule 1-1 moving within the body, detects information of this electric wave (electric wave intensity and/or phase), and transmits this detected information to the HMD 3-1.

Next, in step S212, the position estimation section 37 of the HMD 3-1 estimates the position within the body of the wireless capsule 1-1, based on the electric wave information received from the wireless relay apparatus 2-1.

Next, in step S215, the generation section 34 of the HMD 3-1 determines whether or not the position of the wireless capsule 1-1 estimated by the position estimation section 37 is at an area near the affected part (affected part surroundings).

In the case where it is not at an area near the affected part (S215/NO), in step S218, the generation section 34 of the HMD 3-1 generates control signals which perform instructions so as to move the wireless capsule 1-1 to an area near the affected part, and transmits the generated control signals to the wireless capsule 1-1 via the wireless relay apparatus 2-1. Here, the generation section 34 can shorten the treatment time of the entire body by the wireless capsule 1-1, by generating and transmitting control signals which perform instructions so as to increase the movement speed.

On the other hand, in the case where it is at an area near the affected part (S215/YES), in step S219, the HMD 3-1 acquires a body interior image from the wireless capsule 1-1, and displays the acquired body interior image on the display section 32. Specifically, for example, the generation section 34 of the HMD 3-1 generates control signals which instruct imaging start, and transmits the generated control signals to the wireless capsule 1-1. The imaging section 10 of the wireless capsule 1-1 starts imaging within the body, in accordance with the control signals received from the HMD 3-1, and continuously transmits a body interior image to the HMD 3-1. In this way, the medical practitioner 6 who is wearing the HMD 3-1 can confirm the body interior image of the test subject 5 (patient) in real time, from the wireless capsule 1-1 being brought near to the affected part, and it may not be necessary to continuously confirm a large amount of body interior images from the start of examination. Further, the display control section 30 of the HMD 3-1 may present the position of the wireless capsule 1-1 estimated by the position estimation section 37 along with an internal body map. In this way, the medical practitioner 6 can easily understand what position the wireless capsule 1-1 is at present within the body. Here, a display example of the display section 32 will be described by referring to FIG. 10.

Figure 10:
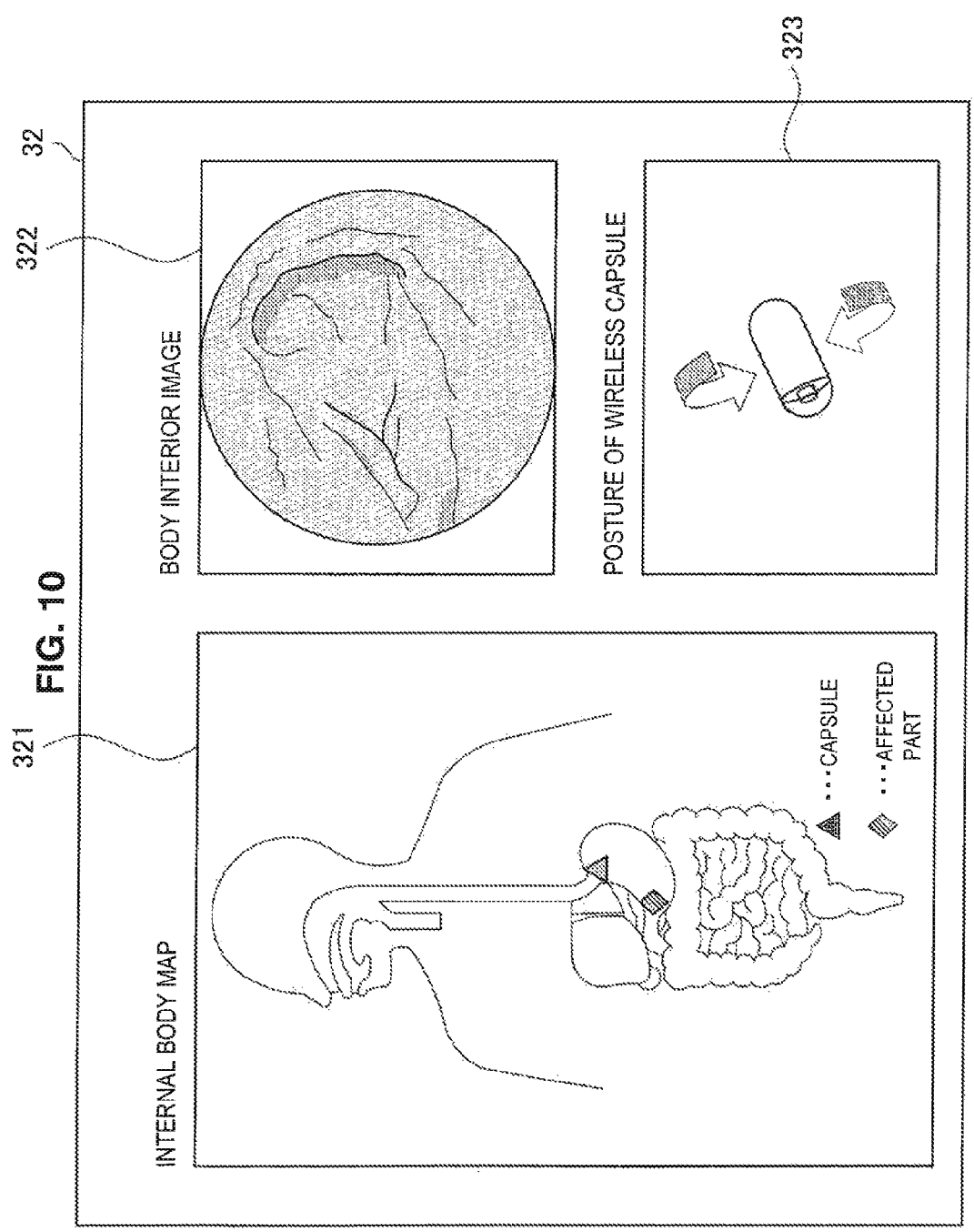
FIG. 10 is a figure for describing an example of a display screen displayed on a display section of the HMD.

FIG. 10 is a figure for describing an example of a display screen displayed on the display section 32 of the HMD 3-1. As shown in FIG. 10, an internal body map 321, a body interior image 322, and a posture presentation image 323 presenting the posture of the wireless capsule 1-1 are included on the display section 32.

The internal body map 321 may be a map image (front view) by the arrangement and size of the internal organs within an average body, or may be a personalized map image (front view) which is generated by performing an actual image scan within the body of the test subject 5 prior to the introduction of the wireless capsule 1-1. Further, as shown in FIG. 10, a mark which shows an affected part, and a mark which shows the present location of the wireless capsule 1-1 are displayed superimposed on the internal body map 321. In this way, the medical practitioner 6 can intuitively understand the present position within the body of the wireless capsule 1-1, and the position of the affected part.

The body interior image 322 is an image continuously transmitted from the wireless capsule 1-1, and the medical practitioner 6 can confirm the body interior image in real time.

The posture presentation image 323 is an image which shows the present posture of the wireless capsule 1-1, based on the posture signals detected by the posture sensor section 33 of the wireless capsule 1-1. The posture presentation image 323 may be generated by a three-dimensional image. Further, the posture of the wireless capsule 1-1 presented by the posture presentation image 323 is a posture with respect to the internal body map 321 (for example, a front view).

Next, in step S221, the HMD 3-1 moves the wireless capsule 1-1 up to the affected part, based on an accurate position of the wireless capsule 1-1. Specifically, the position estimation section 37 of the HMD 3-1 can estimate a more accurate position, by performing an analysis of the body interior image, in addition to information of the beacon electric wave from the wireless capsule 1-1. Then, the generation section 34 of the HMD 3-1 moves the wireless capsule 1-1 up to the affected part, in accordance with such a position which has been more accurately estimated, additionally generates control signals for controlling the posture of the wireless capsule 1-1 (or the imaging section 10 capable of independently performing direction conversion) so that the imaging direction faces the affected part, and transmits the generated control signals.

Further, the HMD 3-1 may generate and transmit control signals for controlling the posture of the wireless capsule 1-1, based on the posture signals detected by the posture sensor section 33 in accordance with movements of the head of the medical practitioner 6. In this way, the medical practitioner 6 can intuitively control the posture of the wireless capsule 1-1, by moving his or her head in the direction which is to be viewed while confirming the body interior image displayed on the display section 32, and the medical practitioner 6 can more accurately move the wireless capsule 1-1 up to the affected part.

Next, in step S224, in the case where the position of the wireless capsule 1-1 has moved near to the affected part, the generation section 34 of the HMD 3-1 generates control signals which perform instructions so as to stop near the affected part, and transmits the generated control signals to the wireless capsule 1-1 via the wireless relay apparatus 2-1. The wireless capsule 1-1 stops near the affected part by the stopping section (not shown in the figures), in accordance with the received control signals. Note that, since the wireless capsule 1-1 does not necessarily have to stop near the affected part according to the contents of the treatment, in this case, the generation section 34 does not generate control signals which instruct stopping. Further, the generation section 34 generates control signals which perform instructions so as to perform a prescribed treatment for the affected part, and transmits the generated control signals to the wireless capsule 1-1 via the wireless relay apparatus 2-1. Further, the control signals of stopping or treatment may be generated at a timing or by content in accordance with instructions by the medical practitioner 6 (user operations input by the operation input section 36).

Next, in step S227, when treatment is completed, the wireless capsule 1-1 ends transmission of the body interior image, and restarts movement within the body by releasing the stop in the case of being stopped near the affected part.

To continue, in step S230, the HMD 3-1 determines whether or not treatment of all the affected parts has been completed, and repeats the above described steps S206 to S227 until treatment of all the affected parts has been completed.

Then, in the case where treatment of all the affected part has been completed (S230/YES), in step S233, the HMD 3-1 performs a control so as to discharge the wireless capsule 1-1 from within the body. Specifically, the generation section 34 of the HMD 3-1 may generate control signals which instruct movement (driving) to a discharge direction and transmit the generated control signals to the wireless capsule 1-1, or generate and transmit control signals which perform instructions so as to end driving (self-propulsion) in the case of being left to natural movements due to peristaltic movements.

Heretofore, the control system (wireless communication system) according to the present embodiment has been specifically described. Note that, the operation processes show in FIG. 8 and FIG. 9 are one example, and the present embodiment is not limited to these operation processes. For example, in the case where an affected part is discovered in the operation processes during examination described by referring to FIG. 8, the stopping and treatment processes may be performed at this location. Further, while the wireless capsule 1-1 according to the above described first embodiment has the electric wave transmission section 16, which transmits only a beacon used as its own position information, separated from the wireless communication section 11, the beacon may be transmitted from the wireless communication section 11. That is, the configuration of the wireless capsule 1-1 according to the first embodiment may have a configuration in which the electric wave transmission section 16 is not separately included, and in this case, a beacon is transmitted from the wireless communication section 11.

3. The Second Embodiment

3-1. Configuration

To continue, an operation system (wireless communication system) according to a second embodiment will be described. While position estimation of the wireless capsule 1-1 is performed in the above described first embodiment by using a beacon transmitted from the electric wave transmission section 16 or the wireless communication section 11 of the wireless capsule 1-1, the control system according to the present embodiment is not limited to this. For example, it is possible for the control system according to the present embodiment to perform position estimation of the wireless capsule 1 even in the case where a beacon is not transmitted. Hereinafter, the case where position estimation of the wireless capsule 1 is performed without using a beacon will be described as the second embodiment.

The control system according to the second embodiment includes a wireless capsule 1-2, a wireless relay apparatus 2-2, and an HMD 3-2. Hereinafter, a configuration of each apparatus which forms the control system according to the present embodiment will be described by referring to FIG. 11 to FIG. 15.

3-1-1. Configuration of the Wireless Capsule

Figure 11:
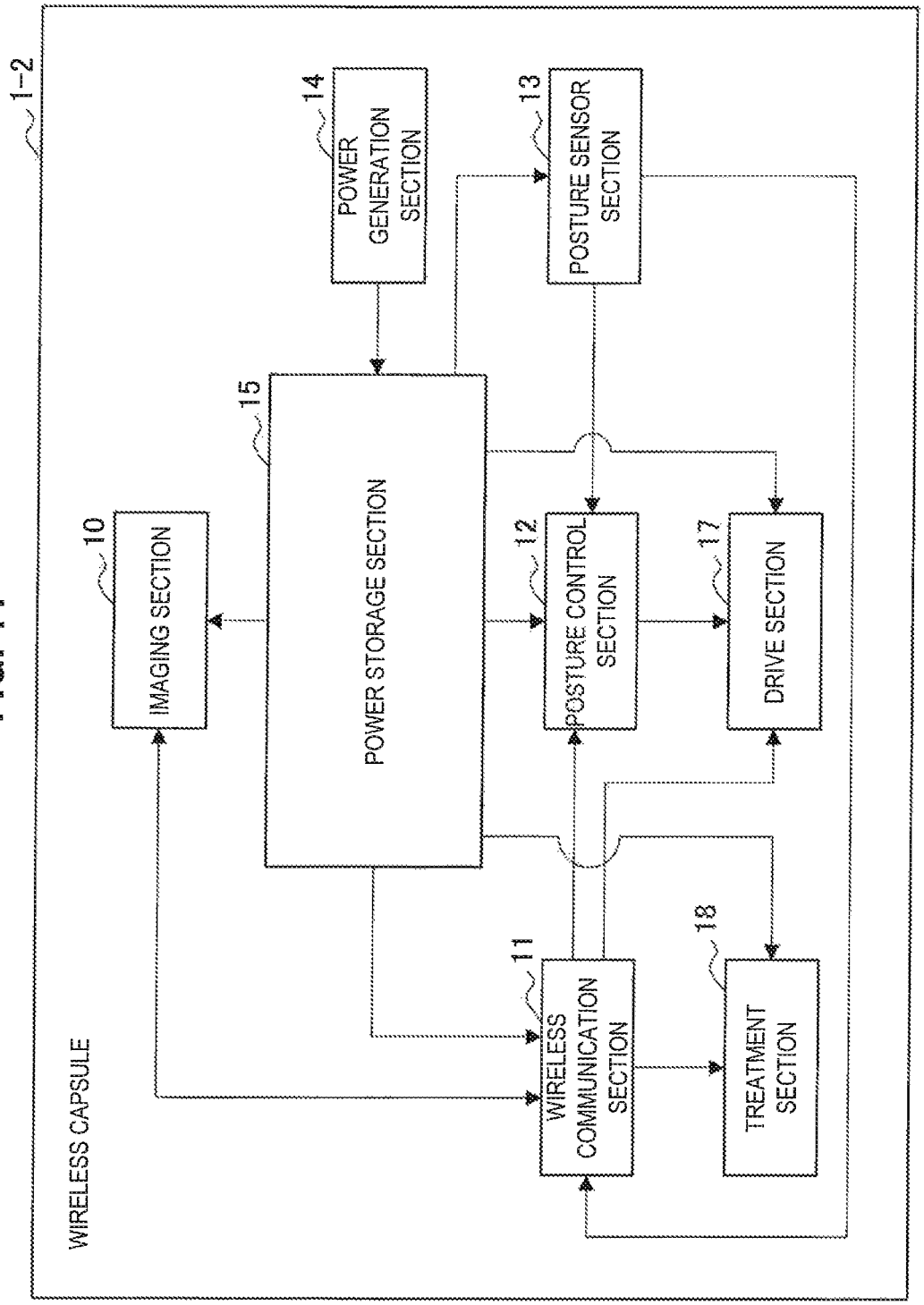
FIG. 11 is a block diagram which shows an example of a configuration of the wireless capsule according to a second embodiment of the present disclosure.

FIG. 11 is a block diagram which shows an example of a configuration of the wireless capsule 1-2 according to the second embodiment. As shown in FIG. 11, the wireless capsule 1-2 according to the present embodiment has an imaging section 10, a wireless communication section 11 (first wireless communication section), a posture control section 12, a posture sensor section 13, a power generation section 14, a power storage section 15, a drive section 17, and a treatment section 18.

When compared to the configuration of the wireless capsule 1-1 according the first embodiment described by referring to FIG. 2, the configuration of the wireless capsule 1-2 according to the present embodiment is different in that is does not have the electric wave transmission section 16.

Further, since each of the elements of the wireless capsule 1-2 are the same as the same elements of the first embodiment, a specific description of these elements will be omitted here.

3-1-2. Configuration of the Wireless Relay Apparatus

Figure 12:
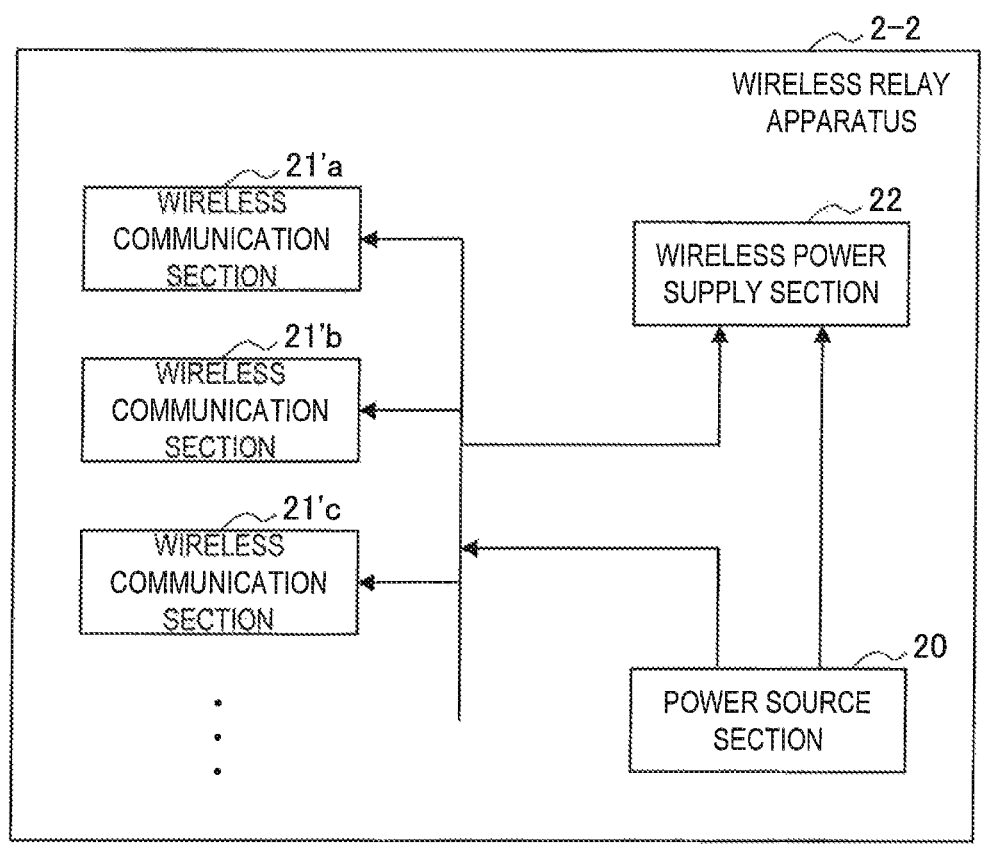
FIG. 12 is a block diagram which shows an example of a configuration of the wireless relay apparatus according to the second embodiment.

FIG. 12 is a block diagram which shows an example of a configuration of the wireless relay apparatus 2-2 according to the second embodiment. As shown in FIG. 12, the wireless relay apparatus 2-2 according to the present embodiment has a power source section 20, a plurality of wireless communication sections 21'*a*, 21'*b* and 21'*c* (hereinafter, called a plurality of wireless communication sections 21'), and a wireless power supply section 22.

Since the power source section 20 and the wireless power supply section 22 are the same as the same elements of the first embodiment, a specific description of these elements will be omitted here.

The plurality of wireless communication sections 21' (third wireless communication sections) are the same as those of the first embodiment in that relay of data communication is performed between the wireless capsule 1-2 and the HMD 3-2. Specifically, the wireless communication sections 21' receive a body interior image from the wireless capsule 1-2 and transmit the received body interior image to the HMD 3-2, and receive control signals from the HMD 3-2 and transmit the received control signals to the wireless capsule 1-2.

Further, the wireless communication sections 21' according to the present embodiment perform mutual transmission and reception of electric waves, and transmit electric wave information (electric wave intensities and/or phases or the like) received by each electric wave to the HMD 3-2. In this way, electric wave propagation characteristics between the plurality of wireless communication sections 21' are measured, and are used when estimating the position of the wireless capsule 1-2 on the HMD 3-2 side.

3-1-3. Configuration of the HMD

Figure 13:
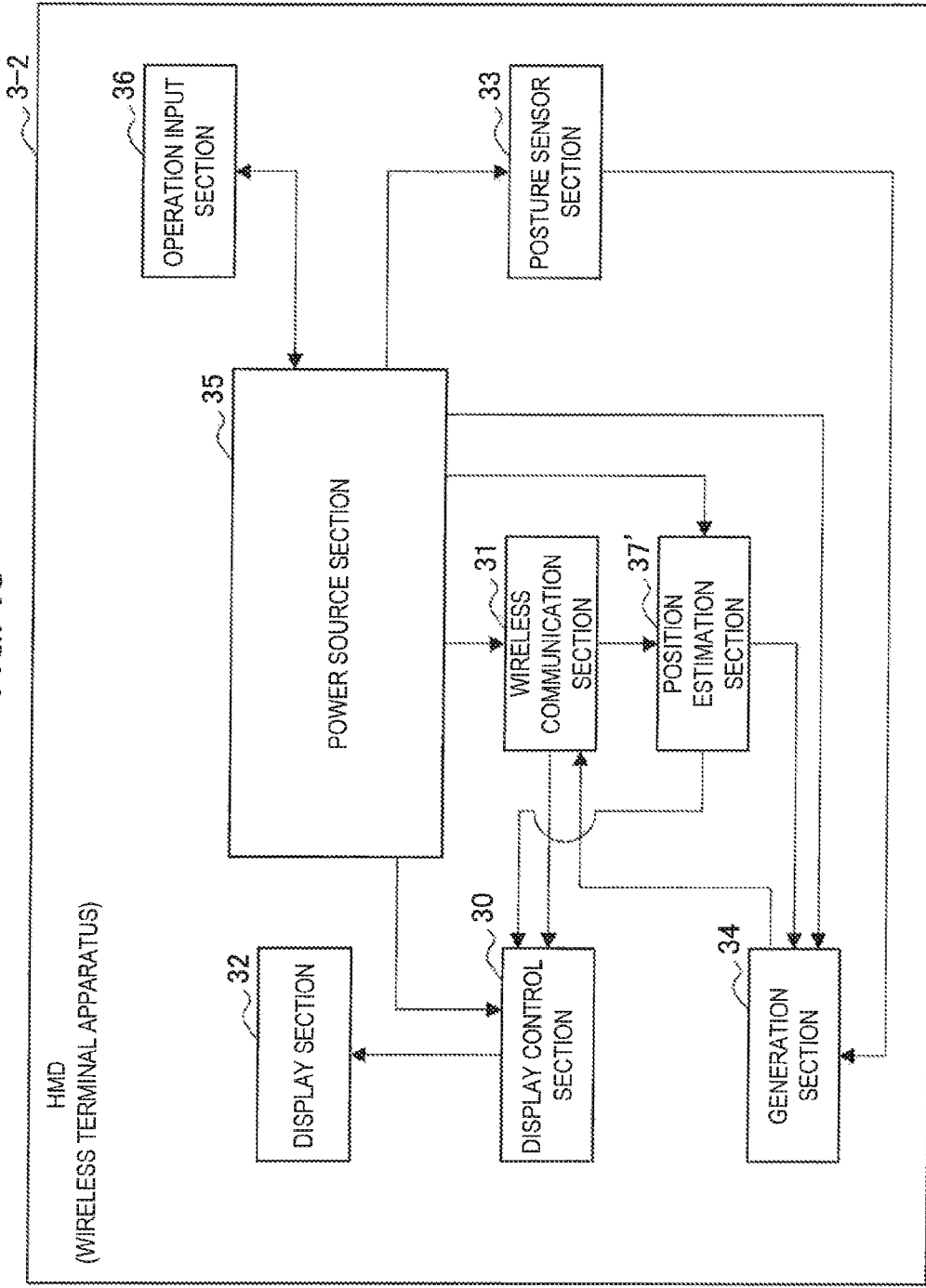
FIG. 13 is a block diagram which shows an example of a configuration of the HMD according to the second embodiment.

FIG. 13 is a block diagram which shows an example of a configuration of the HMD 3-2 according to the second embodiment. As shown in FIG. 13, the HMD 3-2 according to the present embodiment has a display control section 30, a wireless communication section 31 (second wireless communication section), a display section 32, a posture sensor section 33, a generation section 34, a power source section 35, an operation input section 36, and a position estimation section 37'.

When compared to the configuration of the HMD 3-1 according to the first embodiment described by referring to FIG. 6, the configuration of the HMD 3-2 according to the present embodiment is different with regards to the position estimation section 37'. Since each of the elements other than the position estimation section 37' are the same as the same elements of the first embodiment, a specific description of these elements will be omitted here.

The position estimation section 37' estimates the position within the body of the wireless capsule 1-2, based on electric wave information (intensities and/or phases of electric waves or the like) which the wireless communication section 31 has received from the wireless relay apparatus 2-2. Specifically, the wireless communication sections 21' of the wireless relay apparatus 2-2 perform mutual transmission and reception of electric waves, and the position estimation section 37' estimates the position of the wireless capsule 1-2, by using a transfer function within the body corresponding to electric wave propagation characteristics between the plurality of wireless communication sections 21' measured based on information of the received electric waves. Hereinafter, a specific description will be made by referring to FIG. 14.

Figure 14:
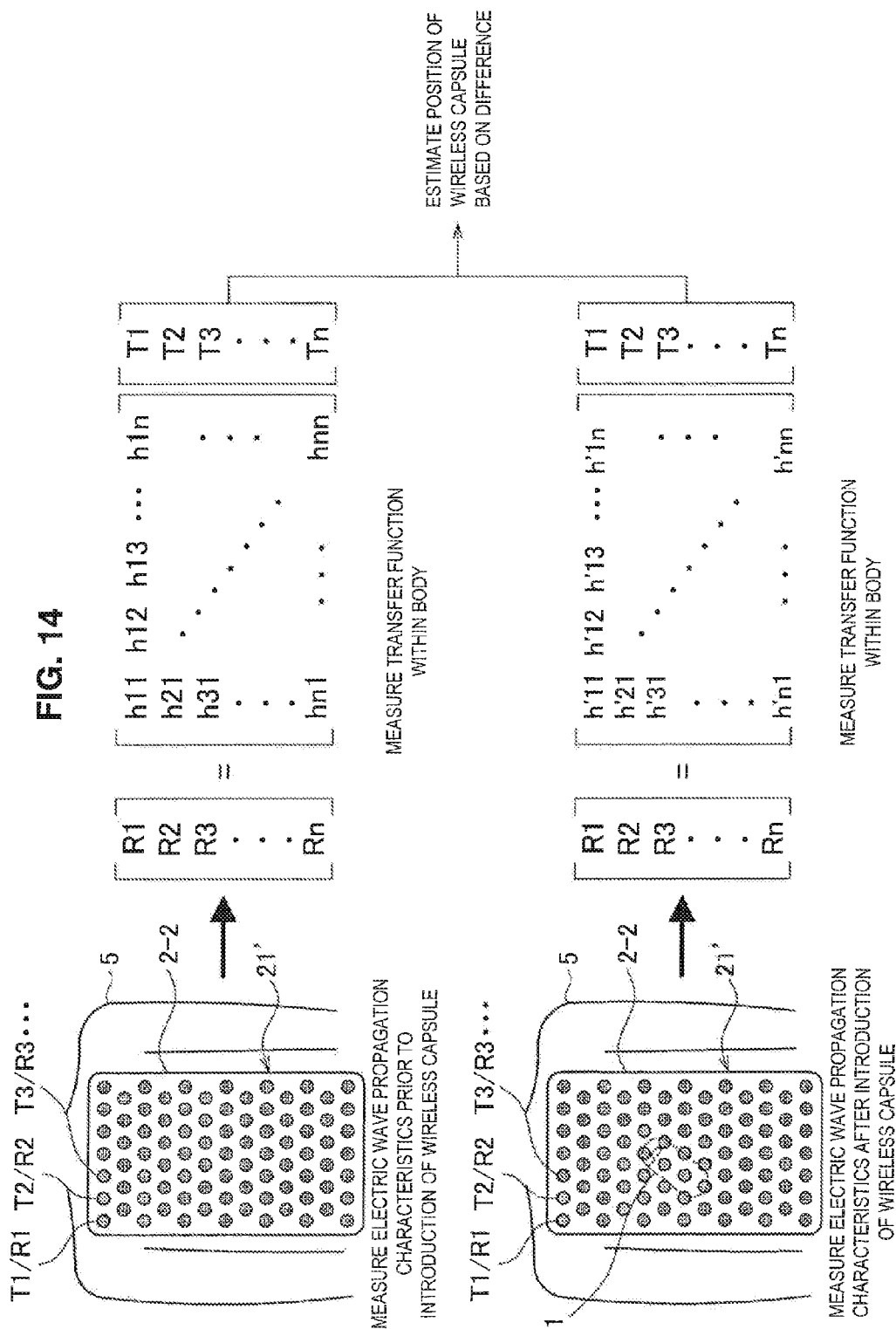
FIG. 14 is a figure for describing a method which estimates the position of the wireless capsule according to the second embodiment.

FIG. 14 is a figure for describing a method which estimates the position of the wireless capsule 1-2 according to the second embodiment. As shown on the top part of FIG. 14, prior to the wireless capsule 1-2 being introduced into the test subject 5, electric wave propagation characteristics between the plurality of wireless communication sections 21' of the wireless relay apparatus 2-2 are measured in advance. As shown in FIG. 14, the plurality of wireless communication section 21' (T1 to Tn) of the wireless relay apparatus 2-2 each transmit electric waves, and electric wave propagation characteristics between the plurality of wireless communication sections 21' are measured based on information of electric waves received by each of the plurality of wireless communication sections 21' (R1 to Rn). Then, a transfer function within the body (prior to the introduction of the wireless capsule 1-2) is measured in accordance with the measured electric wave propagation characteristics.

On the other hand, as shown on the bottom part of FIG. 14, after the wireless capsule 1-2 has been introduced into the test subject 5, electric wave propagation characteristics between the plurality of wireless communication sections 21' of the wireless relay apparatus 2-2 are again measured. As shown in FIG. 14, the plurality of wireless communication sections 21' (T1 to Tn) of the wireless relay apparatus 2-2 each transmitted electric waves, and electric wave propagation characteristics between the plurality of wireless communication sections 21' are measured based on information of electric waves received by each of the plurality of wireless communication sections 21' (R1 to Rn). Then, a transfer function within the body (after the introduction of the wireless capsule 1-2) is measured in accordance with the measured electric wave propagation characteristics.

The position estimation section 37' estimates the position of the wireless capsule 1-2, based on the difference of the transfer function within the body prior to and after the introduction of the wireless capsule 1-2. In this way, the position within the body of the wireless capsule 1-2 can be estimated in the present embodiment, even in the case where a beacon electric wave is not transmitted from the wireless capsule 1-2.

Heretofore, a configuration of each apparatus which forms the control system (wireless communication system) according to the present embodiment has been specifically described. To continue, the operation processes of the control system according to the present embodiment will be described.

<3-2. Operation Processes>

Here, as an example, the operation process in the case where a desired treatment is used during treatment, in the case where the wireless capsule 1-2 has already discovered an affected part (the position of the affected part is already known), will be described by referring to FIG. 15.

Figure 15:
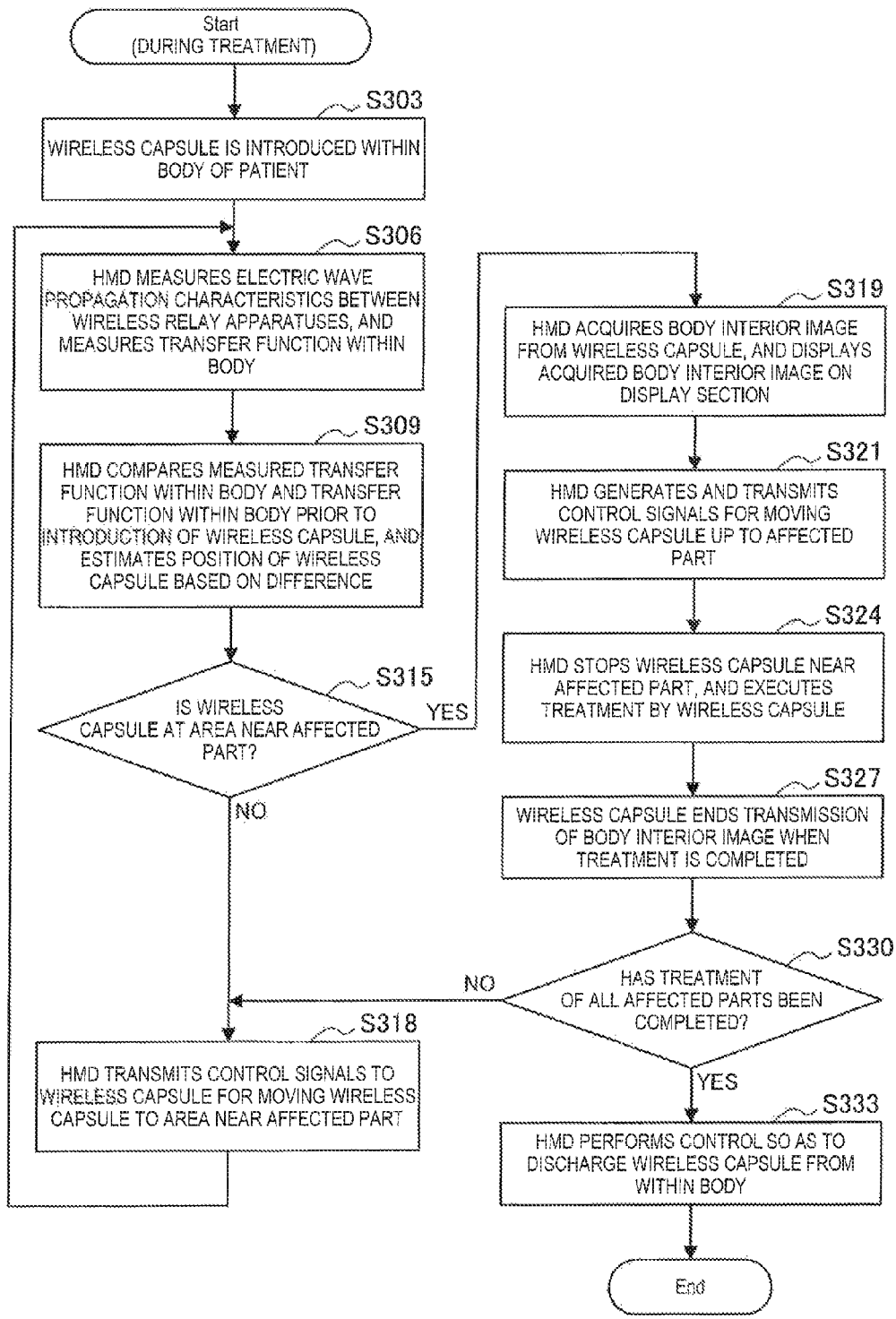
FIG. 15 is a flow chart which shows the operation processes during treatment of the control system according to the second embodiment.

FIG. 15 is a flow chart which shows the operation processes during treatment of the control system according to the second embodiment. As shown in FIG. 15, first in step S303, the wireless capsule 1-2 is introduced within the body of a patient (test subject 5).

Next, in step S306, the HMD 3-2 measures electric wave propagation characteristics between the plurality of wireless communication sections 21' of the wireless relay apparatus 2-2, and measures a transfer function within the body of the test subject 5.

Next, in step S309, the HMD 3-2 compares the measured transfer function within the body, and a transfer function within the body measured in advance prior to the introduction of the wireless capsule 1-2, and estimates the position of the wireless capsule 1-2 based on this difference.

To continue, in steps S315 to S333, processes the same as the processes shown in steps S215 to S233 described by referring to FIG. 9 are performed. Specifically, in step S315, in the case where it is determined that the position of the wireless capsule 1-2 has reached an area near the affected part (S315/YES), to continue in steps S319 to S333, various control signals (posture control signals and treatment control signals) are transmitted from the HMD 3-2 to the wireless capsule 1-2 via the wireless relay apparatus 2-2. In this case, the wireless communication function (function of the wireless communication section 31) of the wireless capsule 1-2 is turned on by a control from the HMD 3-2 (or by having the wireless relay apparatus 2-2 supply power to the wireless capsule 1-2 from instructions by the HMD 3-2), and a beacon may be transmitted from the wireless communication section 31.

Heretofore, the control system according to the second embodiment has been described. In the present embodiment, the position of the wireless capsule 1-2 can be estimated, even in the case where the wireless communication function of the wireless capsule 1-2 has been turned off (the case where a beacon is not transmitting). Further, in the case where an estimated position of the wireless capsule 1-2 is near the affected part (the case where the wireless capsule 1-2 has reached near the affected part), a beacon may be transmitted from the wireless communication section 31 by turning on the wireless communication function, and in this way, the position of the wireless capsule 1-2 can be more accurately understood.

4. Conclusion

As described above, in the control system (wireless communication system) according to an embodiment of the present disclosure, a body interior image is displayed on the HMD 3 (an example of a wireless terminal apparatus) in real time, and the posture of the wireless capsule 1 (specifically, the imaging direction) can be controlled in accordance with movements (changes in posture) of the HMD 3. In this way, for example, by having the medical practitioner 6 who is wearing the HMD 3 simply move his or her head in a direction to be viewed, the medical practitioner 6 can view the body interior image in this direction, and can be intuitively control the posture of the wireless capsule 1.

It should be understood by those skilled in the art that various modifications, combinations, sub-combinations and alterations may occur depending on design requirements and other factors insofar as they are within the scope of the appended claims or the equivalents thereof.

For example, a computer program for causing hardware, such as a CPU, ROM and RAM built into the wireless capsule 1, the wireless relay apparatus 2 or the HMD 3, to exhibit the functions of the above described wireless capsule 1, wireless relay apparatus 2 or HMD 3 can be created. Further, a computer-readable storage medium having this computer program stored therein can also be provided.

Further, it may not be necessary for each step in each of the flow charts to be performed in a time series process, in accordance with the order described in the attached figures. For example, steps S106 and S109 shown in FIG. 8, steps S219 and S221 shown in FIG. 9, or the like may each be performed in parallel.

Additionally, the present technology may also be configured as below.

(1) A wireless communication system including:
  a wireless capsule including
    an imaging section,
    a posture control section,
    a first wireless communication section which transmits an image captured by the imaging section and receives a control signal for controlling the posture control section, and
    a power supply section which supplies power to the imaging and the posture control section; and
  a wireless terminal apparatus including
    a second wireless communication section which receives the image transmitted from the first wireless communication section, and transmits the control
    a display control section which performs a control in a manner that the image is displayed on a display section,
    a posture detection section which detects a posture of the display section, and
    a generation section which generates the control signal based on a posture signal detected by the posture detection section.

(2) The wireless communication system according to (1),
  wherein the wireless terminal apparatus includes a head mounted display, and
  wherein the posture detection section detects a posture signal corresponding to a movement of the head of a user wearing the head mounted display.

(3) The wireless communication system according to (1) or (2),
  wherein the generation section generates the control signal for controlling a posture of the wireless capsule or the imaging section included in the wireless capsule in substantially the same direction as a direction of a change in a posture shown by the posture signal detected by the posture detection section.

(4) The wireless communication system according to any one of (1) to (3),
  wherein the wireless capsule further includes
    an electric wave transmission section which transmits an electric wave, and
    a treatment execution section which applies a treatment to an affected part in accordance with a control signal from outside,
  wherein the wireless communication system further includes:
    a wireless relay apparatus including
      third wireless communication sections which are set at a plurality of prescribed positions on a body surface or within a body, the third wireless communication sections each receiving the electric wave transmitted from the electric wave transmission section, transmitting information of the electric wave to the wireless terminal apparatus, and transmitting a control signal to the wireless capsule in accordance with a control signal received from the wireless terminal apparatus, and
      a wireless power supply section which performs wireless power supply to the wireless capsule,
  wherein the second wireless communication section of the wireless terminal apparatus receives information of an electric wave transmitted from the wireless relay apparatus and the image captured by the imaging section, and transmits a control signal for controlling wireless power supply by the wireless relay apparatus, and
  wherein the generation section estimates a position of the wireless capsule based on the information of the electric wave, and generates a control signal for controlling the treatment execution section in accordance with an estimation result.

(5) The wireless communication system according to (4),
  wherein an estimation of the position of the wireless capsule is performed based on an intensity and/or a phase of an electric wave shown by the information of the electric wave.

(6) The wireless communication system according to (5),
  wherein the information of the electric wave is corrected by using a transfer function within the body measured in advance by measuring electric wave propagation characteristics between the plurality of third wireless communication sections, and then used for the estimation of the position of the wireless capsule.

(7) The wireless communication system according to any one of (1) to (3), further including:
  a wireless relay apparatus including
    third wireless communication sections which are set at a plurality of prescribed positions on a body surface or within a body, the third wireless communication sections each transmitting and receiving an electric wave, transmitting information of the received electric wave to the wireless terminal apparatus, and receiving a control signal from the wireless terminal apparatus, and
    a wireless power supply section which performs wireless power supply to the wireless capsule in accordance with the control signal,
  wherein the second wireless communication section of the wireless terminal apparatus receives information of an electric wave transmitted from the wireless relay apparatus, and transmits a control signal for controlling wireless power supply by the wireless relay apparatus, and
  wherein the generation section estimates a position of the wireless capsule based on the information of the electric wave, and generates a control signal for starting power supply to the wireless capsule in the wireless relay apparatus in accordance with an estimation result.

(8) The wireless communication system according to (7),
  wherein an estimation of the position of the wireless capsule is performed based on a difference between a transfer function within the body measured in advance by measuring electric wave propagation characteristics between the plurality of third wireless communication sections, and a transfer function within the body measured from the electric wave propagation characteristics between the plurality of third wireless communication sections calculated based on the information of the electric wave transmitted from the wireless relay apparatus.

(9) The wireless communication system according to any one of (1) to (8), wherein the wireless capsule further includes at least one or more drive sections for self-propulsion inside a body cavity.

(10) The wireless communication system according to (9), wherein the power supply section of the wireless capsule includes a plurality of power generation sections which generate power by resonating at electric waves of a plurality of different frequencies, wherein the drive sections are a plurality of drive sections which each receive power supply from the plurality of power generation sections, and wherein the wireless power supply section of the wireless relay apparatus independently performs wireless power supply at a plurality of different frequencies for controlling a posture of the wireless capsule or the imaging section in accordance with a control signal received from the wireless terminal apparatus.

(11) A wireless terminal apparatus including:
a wireless communication section which receives an image transmitted from a wireless capsule and transmits a control signal which controls a posture of the wireless capsule;
a display control section which performs a control in a manner that the image is displayed on a display section;
a posture detection section which detects a posture of the display section; and
a generation section which generates the control signal based on a posture signal detected by the posture detection section.

(12) A non-transitory computer-readable storage medium having a program stored therein, the program causing a computer to function as:
a wireless communication section which receives an image transmitted from a wireless capsule, and transmits a control signal which controls a posture of the wireless capsule;
a display control section which performs a control in a manner the image is displayed on a display section;
a posture detection section which detects a posture of the display section; and
a generation section which generates the control signal based on a posture signal detected by the posture detection section.

What is claimed is:

1. A wireless communication system comprising:
a wireless capsule including
an imaging section,
a posture control section configured to control a posture of the wireless capsule or the imaging section within the wireless capsule,
a first wireless communication section which transmits an image captured by the imaging section and receives a control signal for controlling the posture control section, and
a power supply section which supplies power to the imaging section and the posture control section, wherein the power supply section includes a plurality of power generation sections which generate power by resonating at electric waves of a plurality of different frequencies; and
a wireless terminal apparatus including
a second wireless communication section which receives the image transmitted from the first wireless communication section, and transmits the control signal,
a display control section which performs control in a manner that the image is displayed on a display section,
a posture detection section which detects a posture of the display section and generates a posture signal, and
a generation section which generates the control signal based on the posture detected by the posture detection section.

2. The wireless communication system according to claim 1,
wherein the wireless terminal apparatus includes a head mounted display, and
wherein the posture detection section detects a posture signal corresponding to a movement of the head of a user wearing the head mounted display.

3. The wireless communication system according to claim 1,
wherein the generation section generates the control signal for controlling the posture of the wireless capsule or the imaging section included in the wireless capsule in substantially the same direction as a direction of a change in the posture shown by the posture detected by the posture detection section.

4. The wireless communication system according to claim 1,
wherein the wireless capsule further includes
an electric wave transmission section which transmits an electric wave, and
a treatment execution section which applies a treatment to an affected part in accordance with a control signal from outside,
wherein the wireless communication system further comprises:
a wireless relay apparatus including
third wireless communication sections which are set at a plurality of prescribed positions on a body surface or within a body, the third wireless communication sections each receiving the electric wave transmitted from the electric wave transmission section, transmitting information of the electric wave to the wireless terminal apparatus, and transmitting a relay control signal to the wireless capsule in accordance with the control signal received from the wireless terminal apparatus, and
a wireless power supply section which performs wireless power supply to the wireless capsule,
wherein the second wireless communication section of the wireless terminal apparatus receives information of an electric wave transmitted from the wireless relay apparatus and the image captured by the imaging section, and transmits the control signal for controlling wireless power supply by the wireless relay apparatus, and
wherein the generation section estimates a position of the wireless capsule based on the information of the electric wave, and generates a control signal for controlling the treatment execution section in accordance with an estimation result.

5. The wireless communication system according to claim 4,
wherein the estimation of the position of the wireless capsule by the generation section is performed based on an intensity and/or a phase of the electric wave shown by the information of the electric wave.

6. The wireless communication system according to claim 5, wherein the information of the electric wave is corrected by using a transfer function within the body measured in advance by measuring electric wave propagation characteristics between the plurality of third wireless communication sections, and then used for the estimation of the position of the wireless capsule.

7. The wireless communication system according to claim 1, further comprising:
a wireless relay apparatus including
third wireless communication sections which are set at a plurality of prescribed positions on a body surface or within a body, the third wireless communication sections each transmitting and receiving an electric wave, transmitting information of the received electric wave to the wireless terminal apparatus, and receiving a control signal from the wireless terminal apparatus, and
a wireless power supply section which performs wireless power supply to the wireless capsule in accordance with the control signal,
wherein the second wireless communication section of the wireless terminal apparatus receives information of the electric wave transmitted from the wireless relay apparatus, and transmits a control signal for controlling wireless power supply by the wireless relay apparatus, and
wherein the generation section estimates a position of the wireless capsule based on the information of the electric wave, and generates a control signal for starting power supply to the wireless capsule in the wireless relay apparatus in accordance with an estimation result.

8. The wireless communication system according to claim 7,
wherein the estimation of the position of the wireless capsule by the generation section is performed based on a difference between a transfer function within the body measured in advance by measuring electric wave propagation characteristics between the plurality of third wireless communication sections, and a transfer function within the body measured from the electric wave propagation characteristics between the plurality of third wireless communication sections calculated based on the information of the electric wave transmitted from the wireless relay apparatus.

9. The wireless communication system according to claim 1,
wherein the wireless capsule further includes one or more drive sections for self-propulsion inside a body cavity.

10. The wireless communication system according to claim 9,
wherein the one or more drive sections are a plurality of drive sections which each receive power supply from the plurality of power generation sections, and
wherein a wireless power supply section of a wireless relay apparatus independently performs wireless power supply at a plurality of different frequencies for controlling the posture of the wireless capsule or the imaging section in accordance with the control signal received from the wireless terminal apparatus.

11. A wireless terminal apparatus comprising:
a wireless communication section which receives an image transmitted from a wireless capsule and transmits a control signal which controls a posture of the wireless capsule;
a display control section which performs a control in a manner that the image is displayed on a display section;
a posture detection section which detects a posture of the display section; and
a generation section which generates the control signal based on a posture signal detected by the posture detection section,
wherein the control signal controls a power supply section of the wireless capsule which generates power for the posture control and includes a plurality of power generation sections which generate power by resonating at electric waves of a plurality of different frequencies.

12. A non-transitory computer-readable storage medium having a program stored therein, the program causing a computer to function as:
a wireless communication section which receives an image transmitted from a wireless capsule, and transmits a control signal which controls a posture of the wireless capsule;
a display control section which performs a control in a manner the image is displayed on a display section;
a posture detection section which detects a posture of the display section; and
a generation section which generates the control signal based on a posture signal detected by the posture detection section,
wherein the control signal controls a power supply section of the wireless capsule which generates power for the posture control and includes a plurality of power generation sections which generate power by resonating at electric waves of a plurality of different frequencies.

* * * * *